(12) United States Patent
Emanuelli et al.

(10) Patent No.: US 11,576,758 B2
(45) Date of Patent: *Feb. 14, 2023

(54) SIMULATION METHOD AND SYSTEM FOR AN OPTIMIZED IMPLANT SITE

(71) Applicants: Silvio Franco Emanuelli, Sanremo (IT); Federico Manes, Sanremo (IT)

(72) Inventors: Silvio Franco Emanuelli, Sanremo (IT); Federico Manes, Sanremo (IT)

( * ) Notice: Subject to any disclaimer, the term of this patent is extended or adjusted under 35 U.S.C. 154(b) by 0 days.

This patent is subject to a terminal disclaimer.

(21) Appl. No.: 17/152,291

(22) Filed: Jan. 19, 2021

(65) Prior Publication Data

US 2021/0137654 A1    May 13, 2021

Related U.S. Application Data

(63) Continuation of application No. 16/486,484, filed as application No. PCT/IB2018/050936 on Feb. 15, 2018, now Pat. No. 10,912,633.

(30) Foreign Application Priority Data

Feb. 17, 2017    (IT) .................. 102017000017965

(51) Int. Cl.
*A61C 13/00* (2006.01)
*G06T 17/00* (2006.01)

(52) U.S. Cl.
CPC .......... *A61C 13/0004* (2013.01); *G06T 17/00* (2013.01); *G06T 2210/41* (2013.01)

(58) Field of Classification Search
CPC .......... A61C 13/0004; A61C 2007/004; G06T 17/00; G06T 2210/41
See application file for complete search history.

(56) References Cited

U.S. PATENT DOCUMENTS 8,562,338 B2 * 10/2013 Kitching ............... A61C 7/002
                                                                433/24
9,111,372 B2 *  8/2015 Ortega ................... G06T 19/00
(Continued)

FOREIGN PATENT DOCUMENTS

DE    102014215103 A1    2/2016
EP         1449489 A1    8/2004
(Continued)

OTHER PUBLICATIONS

Avrampou, et al., "Virtual Implant Planning in the Edentulous Maxilla: Criteria for Decision Making of Prosthesis Design", Clinical Oral Implants Research, vol. 24, 2013, pp. 152-159.
(Continued)

*Primary Examiner* — Said Broome
(74) *Attorney, Agent, or Firm* — Condo Roccia Koptiw LLP

(57) ABSTRACT

The invention describes a computer-implemented method and an optimized implant site simulation system which performs a simulation of a damaged oral cavity of a patient and defines an implant site adapted to receive a dental implant to repair the damage observed. The invention further describes the optimized implant site simulated (SI) and a dental implant (ID) couplable to the optimized implant site (SI) simulated. The invention further describes a computer program to perform the steps of the method and an optimized implant site (SI) simulation system.

20 Claims, 12 Drawing Sheets

(56) References Cited

U.S. PATENT DOCUMENTS

| | | | |
|---|---|---|---|
| 9,411,910 B2* | 8/2016 | Methot | A61C 5/77 |
| 9,566,137 B2* | 2/2017 | Hehn | A61C 9/0053 |
| 11,045,293 B2* | 6/2021 | Fisker | A61C 9/0053 |
| 2007/0099147 A1* | 5/2007 | Sachdeva | A61C 9/0046 433/24 |
| 2009/0111071 A1 | 4/2009 | Yau et al. | |
| 2009/0325127 A1* | 12/2009 | Kusch | A61C 13/0004 700/98 |
| 2011/0136080 A1 | 6/2011 | Holzner et al. | |
| 2012/0203366 A1 | 8/2012 | Saliger et al. | |
| 2012/0239364 A1 | 9/2012 | Glor et al. | |
| 2012/0282567 A1 | 11/2012 | Nilsson | |
| 2014/0234803 A1 | 8/2014 | Hehn | |
| 2014/0329194 A1 | 11/2014 | Sachdeva et al. | |
| 2014/0342302 A1 | 11/2014 | Kopelman et al. | |
| 2018/0206949 A1 | 7/2018 | Thorsten et al. | |

FOREIGN PATENT DOCUMENTS

| | | |
|---|---|---|
| EP | 2322114 A1 | 5/2011 |
| JP | 2005-168518 A | 6/2005 |
| KR | 2014-0005337 A | 1/2014 |
| TW | 201108995 A | 3/2011 |
| WO | 99/26540 A1 | 6/1999 |
| WO | 2007/009719 A1 | 1/2007 |
| WO | 2012/004937 A1 | 1/2012 |

OTHER PUBLICATIONS

Block, Micael S., "Dental Implants: The Last 100 Years", CrossMark, Journal of Oral and Maxillofacial Surgery, vol. 76, No. 1, 2018, pp. 11-26.

Buser, et al., "Optimizing Esthetics for Implant Restorations in the Anterior Maxilla: Anatomic and Surgical Considerations", The International Journal of Oral & Maxillofacial Implants, 2004, pp. 43-61.

Moon, et al., "Clinical Problems of Computer-Guided Implant Surgery", Maxillofacial Plastic and Reconstructive Surgery, vol. 38, No. 1, 2016, pp. 1-6.

Rajput, et al., "A Brief Chronological Review of Dental Implant History", International Dental Journal of Students Research, vol. 4, No. 3, Oct. 2016, pp. 105-107.

Rojas-Vizcaya, Fernando, "Biological Aspects as a Rule for Single Implant Placement. The 3A-2B Rule: A Clinical Report", Journal of Prosthodontics, vol. 22, No. 7, 2013, pp. 575-580.

* cited by examiner

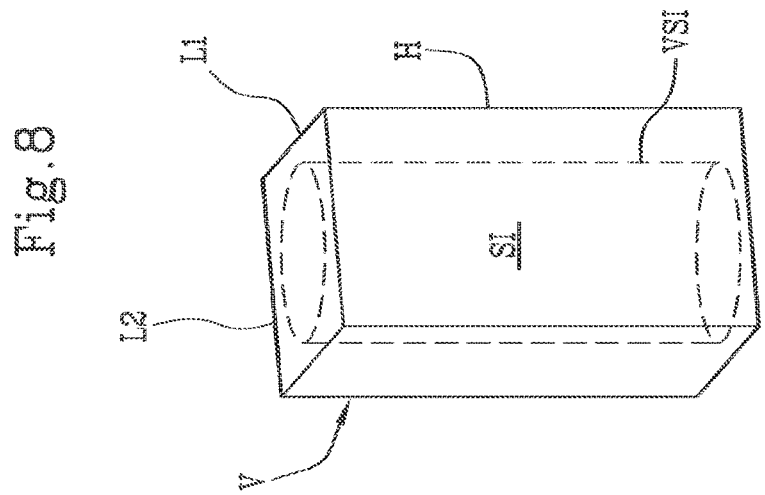
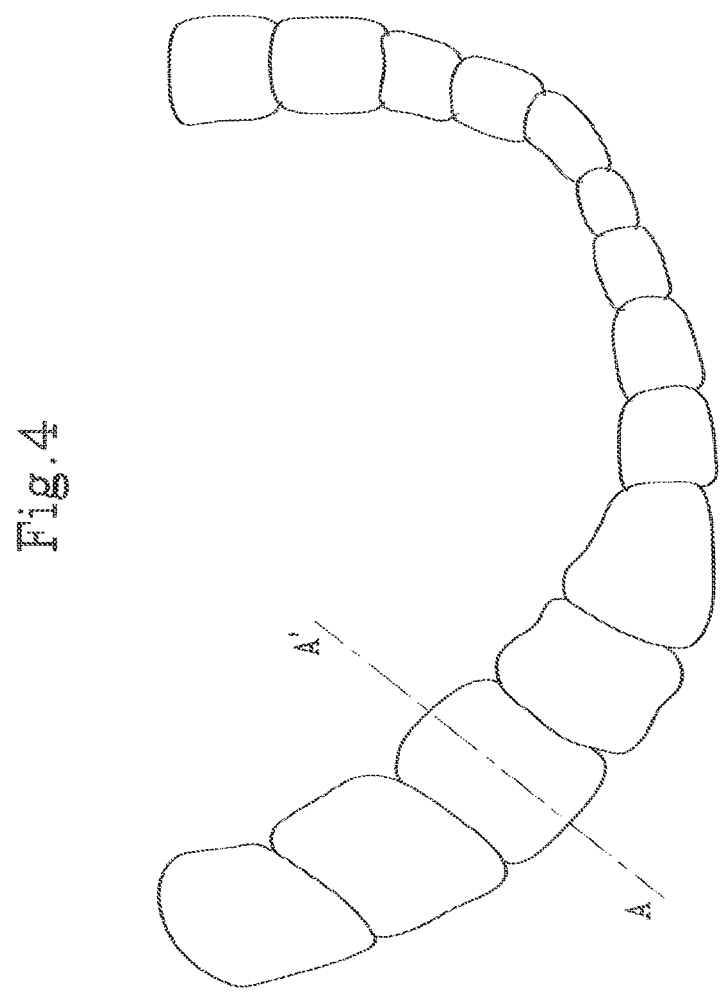

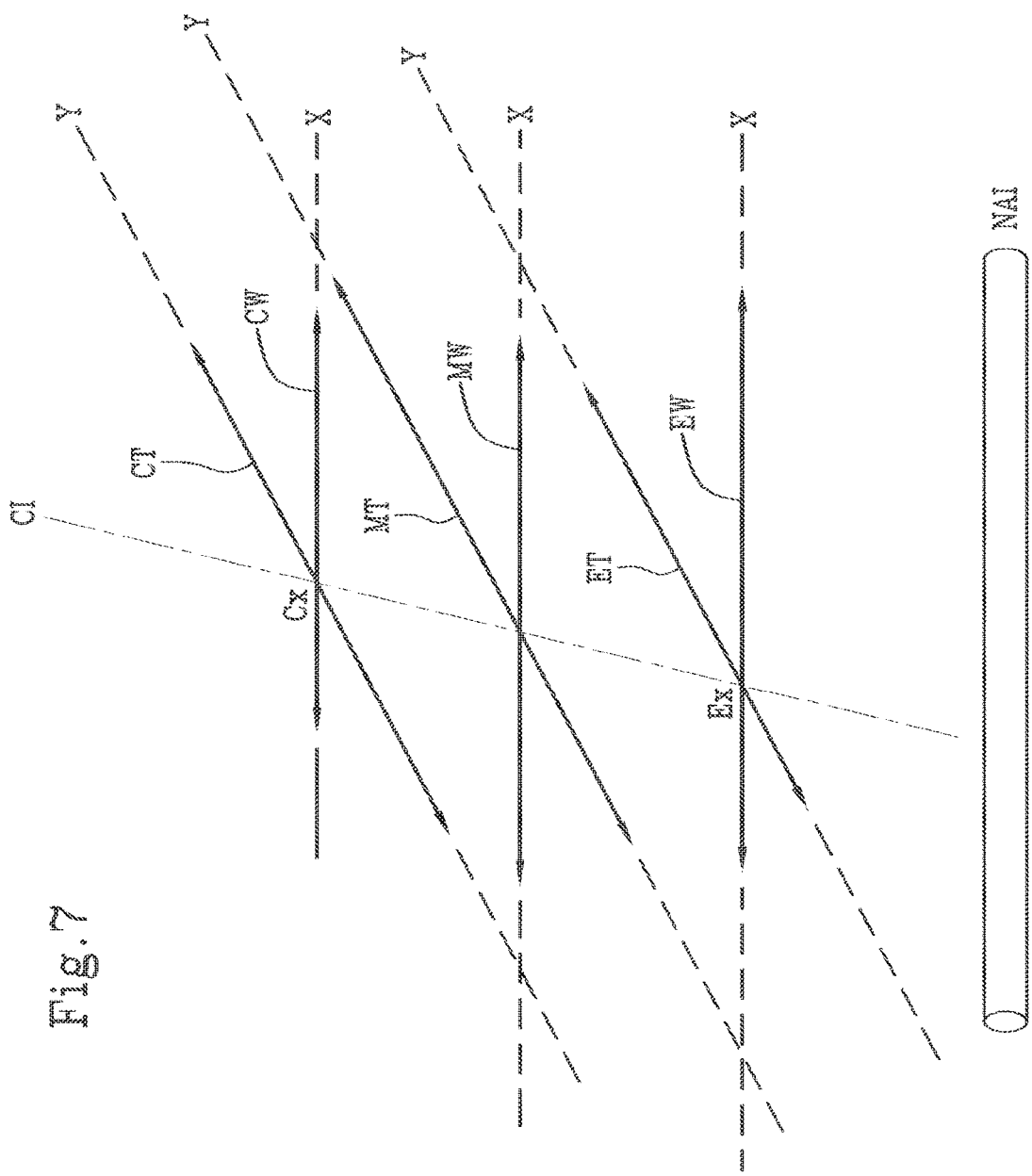
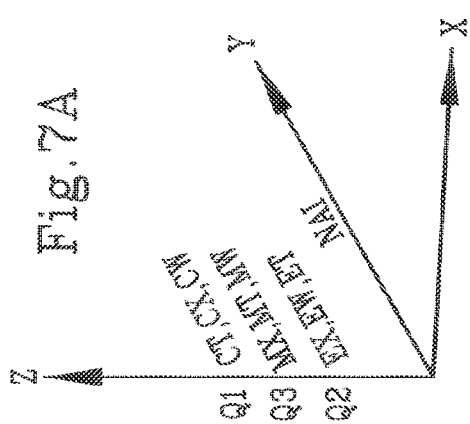

CASE I GH>S_GH

CASE II GH<S_GH

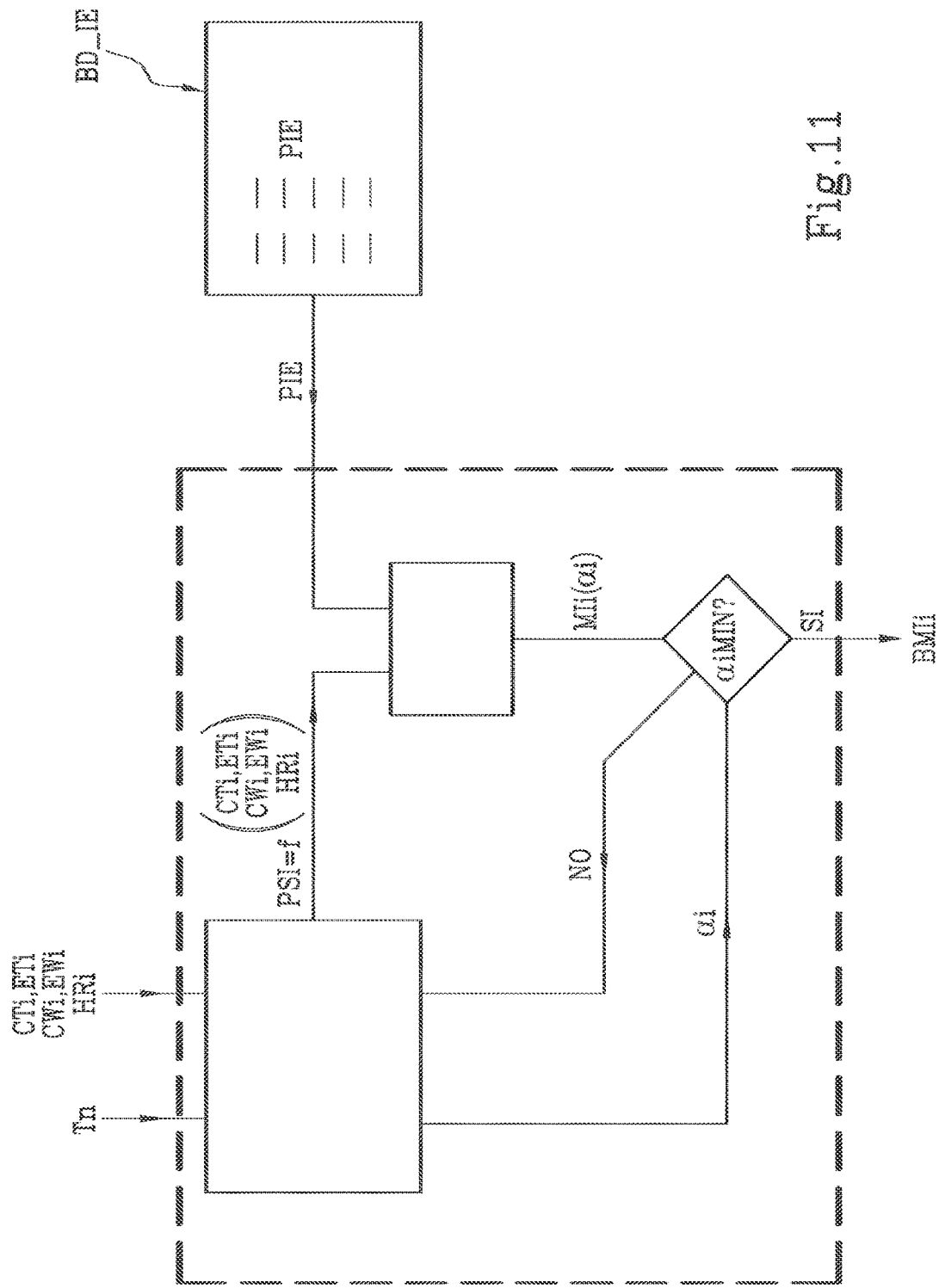

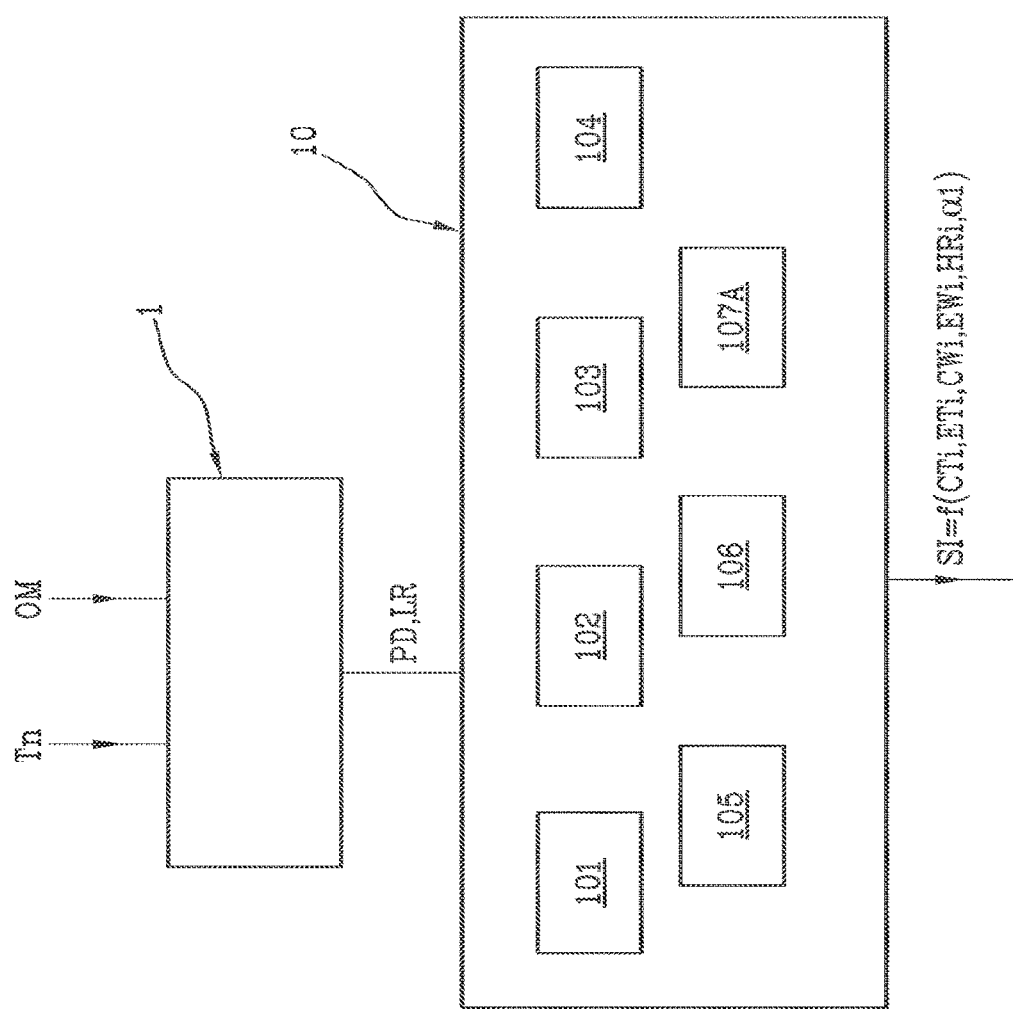

SIMULATION METHOD AND SYSTEM FOR AN OPTIMIZED IMPLANT SITE

CROSS REFERENCE TO RELATED APPLICATIONS

This application is a continuation of U.S. patent application Ser. No. 16/486,484, filed Aug. 15, 2019, which is a National Stage Entry under 35 U.S.C. § 371 of Patent Cooperation Treaty Application No. PCT/IB2018/050936, filed Feb. 15, 2018, which claims priority from Italian Patent Application No. 102017000017965, filed Feb. 17, 2017, the contents of which are hereby incorporated by reference herein.

This application is related to U.S. patent application Ser. No. 16/486,513 filed Aug. 16, 2019, and entitled "A METHOD AND SYSTEM OF IDENTIFYING A DENTAL IMPLANT FOR AN OPTIMIZED IMPLANT SITE," and U.S. patent application Ser. No. 16/486,524 filed Aug. 16, 2019, and entitled "SYSTEM AND METHOD FOR MONITORING OPTIMAL DENTAL IMPLANTS COUPLEABLE WITH AN OPTIMIZED IMPANT SITE," which are hereby incorporated by reference herein.

FIELD OF THE INVENTION

The present invention relates to a computer-implemented method for simulating an optimized implant site.

The present invention further relates to a simulation system for an optimized implant site.

The present invention particularly relates to an optimized implant site simulation method/system for a dental implant starting from simulations of an edentulous site anatomy of a dental prosthesis intended to be coupled to the dental implant.

More particularly, the present invention relates to an optimized implant site simulation method/system within a maxillary arch of the patient's oral cavity as a result of a missing tooth, wherein the following description refers to this field of application for the sole purpose of simplifying the inventive exposure.

It is understood that a simulation of an implant site in another area of the oral cavity and for a different type of tooth falls within the scope of the present invention.

It is further understood that the simulation of the system/method of the invention forms the basis of a simulation addressed to multiple implant sites.

BACKGROUND

At present, dental implants are designed and prepared based on the dentist's instructions basically deriving from the experience gained.

Some guidelines recommend rather trivial criteria for defining the characteristic parameters of dental implants to be applied to patients.

Purpose of the present invention is to provide an exact simulation method of the implant site in terms of conformation of the site itself and in accordance with existing guidelines.

Another object of the present invention is to provide a simulation method of the implant site ensuring durability of the dental implant to be installed in particular upon changing of specific simulation parameters.

SUMMARY

The invention confers the main technical effect arising from the simulation of a specific implant site in terms of sizing and location.

In particular, the invention as described achieves the technical effects of: simulating a specific implant site in terms of structure and design; simulating an objective implant site in terms of design; simulating an implant site ensuring stability to the dental implant to be installed, in particular upon changing of specific simulation parameters; easy simulation of an implant site; and identifying an implant site in accordance with guidelines and suitable to the anatomy and proposed treatment in respect to optimal dental implants available.

It should be noted that the simulation system/method of the invention cannot be performed by purely mental or mathematical means, nor by the thought process that led to the simulation method.

The simulation performed by the invention achieves technical functions typical of modern engineering work. It provides for realistic prediction of the performance of a dental implant in respect to the designed implant site which shall accommodate the former, and thereby ideally allows the dental implant to be developed so accurately such that a prototype's chances of success can be assessed before it is built.

The technical result increases with the speed of the simulation method, as this enables a wide range of designs to be virtually tested and examined for suitability before the expensive implant fabrication process starts.

Without a suitable technical support, an advanced test on a complex dental implant and/or a careful selection among many different projects would not be possible, or at least not feasible within a reasonable time.

It follows that computer-implemented simulation methods for virtual testing represent a practical and practice-oriented part of the dentist's or healthcare professional's or treatment provider's toolkit. What makes them so important is the fact that there is not a purely mathematical, theoretical or mental method which is capable of providing a complete and/or fast prediction of a dental implant performance according to the parameters of the invention, that is different or diversifiable for each single patient. The technical effects and/or advantages already mentioned as well as further technical effects and/or advantages of the invention, will become more apparent from the description made hereafter of an illustrative embodiment described by way of non-limiting example with reference to the accompanying drawings.

BRIEF DESCRIPTION OF THE DRAWINGS

FIG. 4 is a schematic view of the sectional view of FIG. 2.

FIG. 7 is a schematic view of representative measurements of the mandibular bone with respect to an ideal surgical axis.

FIG. 7A shows a reference system for the measurements of FIG. 7.

FIG. 8 is a view of a representative volume of an implant site for the dental implant of FIG. 1.

FIG. 11 is a block diagram of some steps of the inventive method.

FIG. 13 is a block diagram of the optimized implant site simulation system.

DETAILED DESCRIPTION

Figure 1:
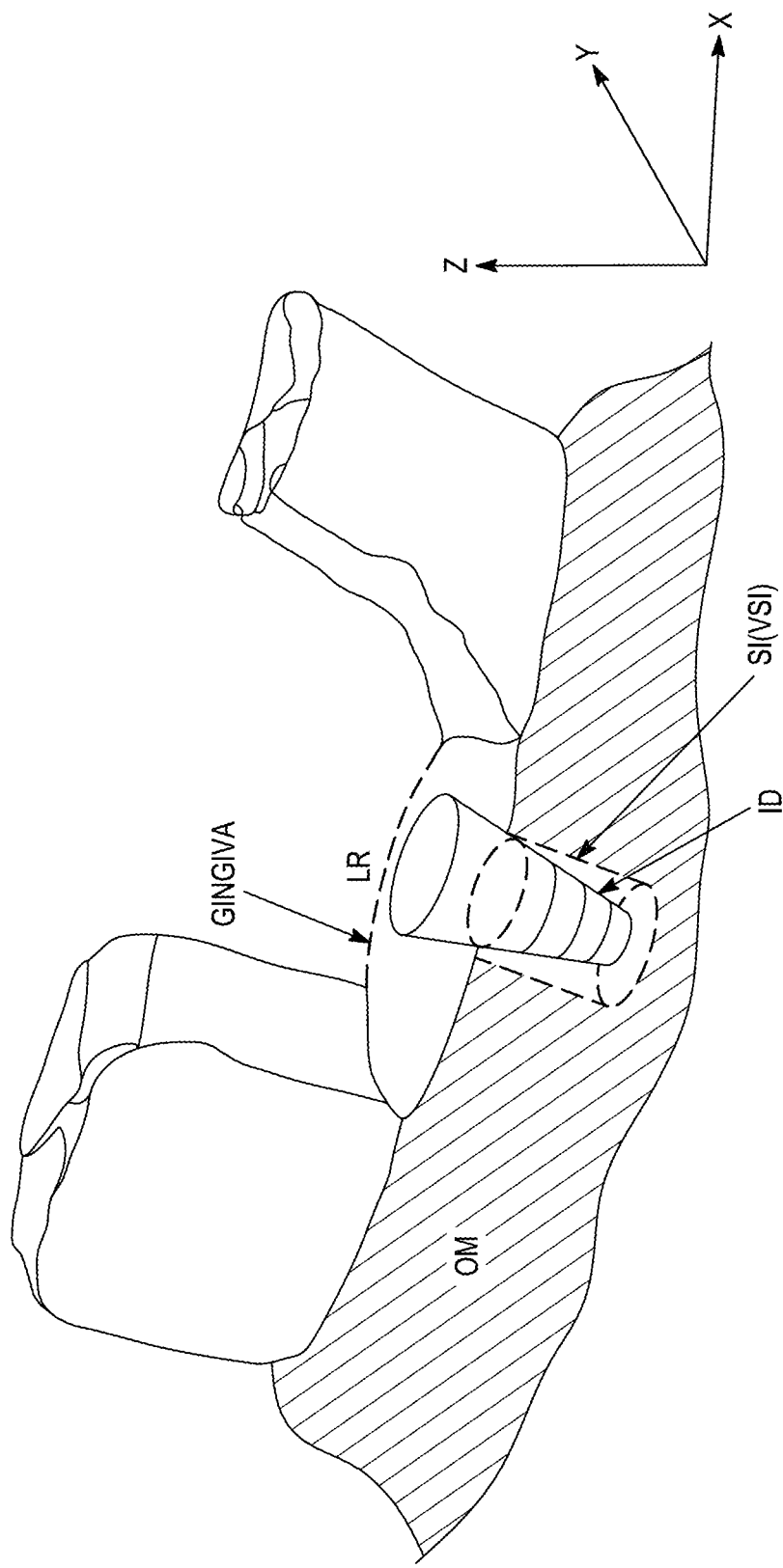
FIG. 1 is a schematic view of a dental implant within the maxillary arch according to the present invention.

The invention describes a simulation method and system for an optimized implant which performs a simulation of a patient's damaged oral cavity and defines an implant site capable of receiving a dental implant aimed at repairing the damage observed. In addition, the invention enables identifying a dental problem as well assimilating an implant site which is dimensioned and configured such as to accommodate a dental implant capable of solving the problems highlighted.

The terminology as described hereinafter will be used several times and maintained as a reference in the appended claims as follows: dental implant=screw inserted into the mandibular and/or maxillary bone; implant site=cavity afforded within the mandible and/or maxilla which accommodates the dental implant; abutment=pin which is coupled to the free end of the dental implant; crown=tooth-shaped cover coupled to the free end of the abutment; dental prosthesis=set of abutment and crown; edentulous site=volumetric space intended to receive the dental prosthesis, in particular space between two existing teeth; vestibule=space between the cheeks and the gingiva; mandible=bone which forms the lower scaffold of the mouth, it accommodates the lower teeth in the maxillary arch, and is the only movable part of the face; maxilla=bone which forms the upper scaffold of the mouth and accommodates the upper dental arch. Unlike the mandible, the maxilla is a fixed bone, which does not move with the opening and closing of the mouth. Overall, the two bones are also referred to as maxillary bones and in the present description the term maxillary bone (OM), will be used in this respect, i.e., without excluding that the example according to which a dental prosthesis is applied to the lower arch excludes the application to the upper arch.

In the description, it will be illustrated by way of example the case of a dental prosthesis PD applied in replacement of a premolar tooth of the maxillary arch, without the invention having to be construed as limited to this example; indeed the method herein described may be also applied where other teeth, such as molars, canines, incisors etc. are to be replaced and moreover on a different arch.

In a first aspect, the invention describes a simulation method of an implant site. The simulation performed by the invention achieves technical functions typical of modern engineering work. It provides for realistic prediction of the performance of a dental implant in respect to the designed implant site which shall accommodate the former, and thereby ideally allows the dental implant to be developed so accurately such that a prototype's chances of success can be assessed before it is built.

The technical result increases with the speed of the simulation method, as this enables a wide range of designs to be virtually tested and examined for suitability before the expensive implant fabrication process starts. Without a suitable technical support, an advanced test on a complex dental implant and/or a careful selection among many different projects would not be possible, or at least not feasible within a reasonable time.

It follows that computer-implemented simulation methods for virtual testing represent a practical and practice-oriented part of the dentist's or healthcare professional's or treatment provider's toolkit. What makes them so important is the fact that there is not a purely mathematical, theoretical or mental method which is capable of providing a complete and/or fast prediction of a dental implant performance according to the parameters of the invention, that is different or diversifiable for each single patient. With particular reference to FIGS. 1 to 5, the simulation method of an implant site SI provides an initial step f1 of graphic simulation.

Figure 2:
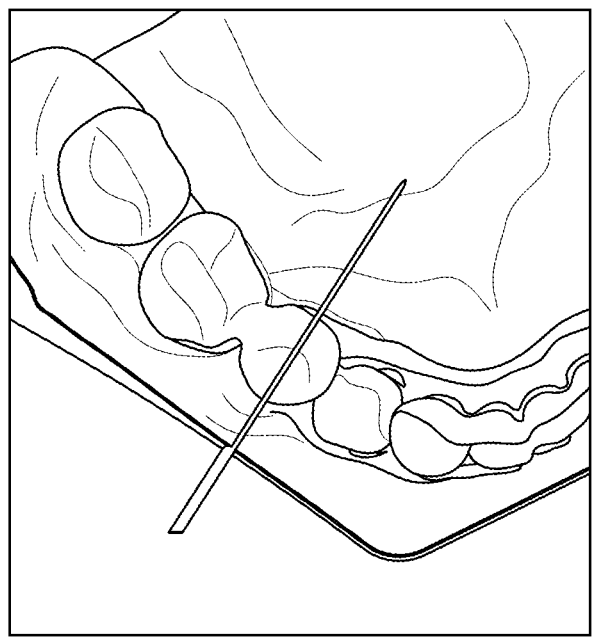
FIG. 2 shows a screenshot of a software simulation of a dental prosthesis and maxillary arch thereof in top plan view.

In particular, FIGS. 2 and 4 respectively show a software simulation screen shot in plan view and a corresponding schematic view used for the present description. More specifically, FIG. 4 is a view of a portion of the maxillary arch of a patient, wherein a missing premolar tooth has been graphically simulated, and wherein an axis A-A' is represented in the simulated premolar, which is adapted to ideally dissect it transversely with respect to the mandibular bone.

Figure 3:
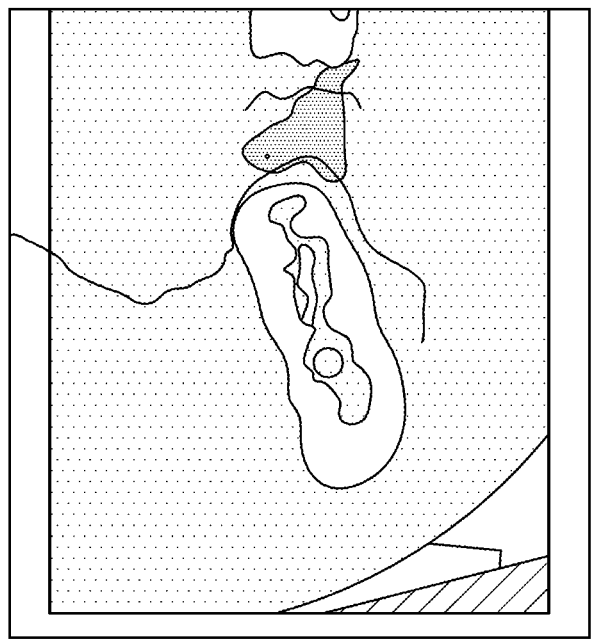
FIG. 3 shows a screenshot of a software simulation of a dental prosthesis and maxillary arch thereof in sectional view along a plane transverse to a provided dental prosthesis.
Figure 5:
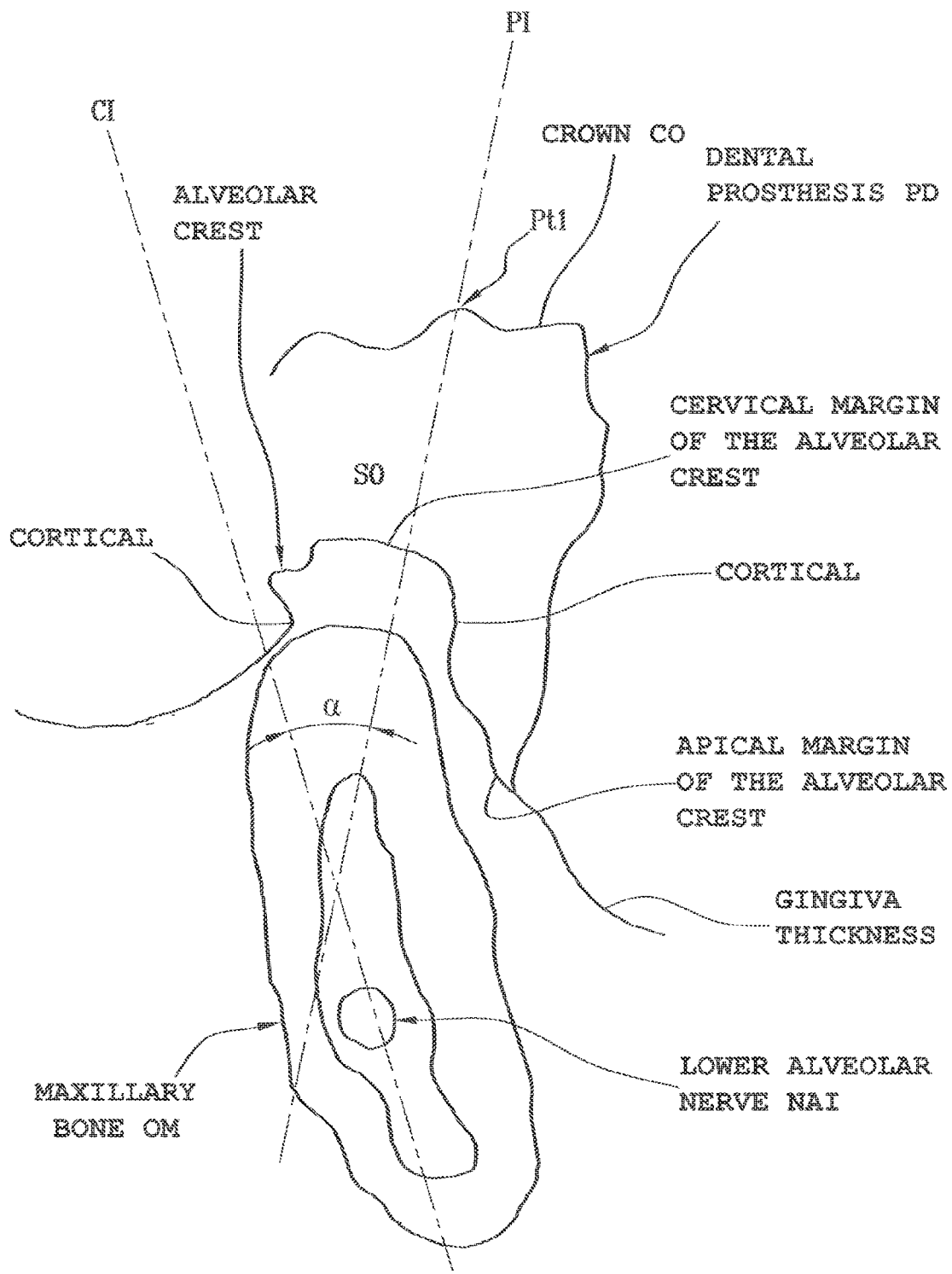
FIG. 5 is a schematic view of the sectional view of FIG. 3.

In particular, FIG. 3 depicts one of a software simulation screenshot in sectional view, whereas FIG. 5 shows a corresponding schematic view used for the present description. In particular, FIG. 5 is a sectional view along the axis A-A' of FIG. 4 of a mandibular bone and the simulated dental prosthesis, wherein there are shown a surgical ideal axis CI and an ideal prosthetic axis PI.

The graphic simulation step f1 according to the invention, allows to graphically simulate an anatomy of a provided dental prosthesis PD (FIG. 5) and a respective edentulous site LR (FIG. 1) corresponding to an identified tooth Tn, wherein the provided dental prosthesis PD is coupled to a dental implant ID (FIG. 1). More generally, the invention is applicable both in the case in which the Tn tooth is missing in the edentulous site, as well as in the case in which the Tn tooth is present in the edentulous site and needs to be rehabilitated. As shown in FIG. 1, the ID dental implant is installed in a maxillary bone OM at the base of the edentulous site LR, in a position occupied by the identified tooth Tn, wherein Tn is the tooth identified in conditions of integrity of the patient's mouth.

Preferably, the graphic simulation step f1 is performed by way of a computed tomography (TAC) of the oral cavity that provides data based on which a 3D reconstruction of the maxillary bones may be effected. Alternatively or in addition, the graphic simulation is achieved by means of a conventional dental prosthesis model, which may also be obtained by intra or extra-oral scanning or virtually modeled. An integrated graphical simulation is achieved by combining the intra or extra-oral scanning, or virtually derived scanning, with the 3D reconstruction made via the computed tomography. Worded differently and in sum, the graphic simulation step f1 is carried out via computer-implemented graphic simulation means, in particular via a computer-implemented graphic simulation apparatus.

All the processing carried out are feasible starting from the first simulation step f1, without which it would not be possible any precise detection of the state of the oral cavity; non-automated detections, based essentially on the clinician's clinical expertise, are fully inappropriate for the subsequent steps of the simulation and can in no way lead to obtaining an optimized implant site. In other words, the first simulation step f1 defines a computer-implemented mathematical graphic model based on which it is possible to perform innovative processing of the invention in order to obtain an accurate and optimized simulation in terms of implementation of an implant site; the implant site thus obtained will be configured for being coupled with a corresponding dental implant.

In a particular example of the graphic simulation of FIG. 2 and the corresponding schematic view of FIG. 4, a premolar tooth that will be added to the patient is shown sectioned by an A-A' axis. In particular, from the graphic simulation of FIG. 3 and the corresponding schematic view of FIG. 5, there is shown the crown CO of the dental prosthesis PD and the maxillary bone OM which tends to white color where the bone is cortical, while tending to gray color where the bone is spongy; in the lower part of the maxillary bone, the lower maxillary nerve NAI is also present.

Starting from the data obtained from the simulation, the inventive method allows an assessment of the actual amount of the maxillary bone OM present at the edentulous site LR. The technical effect achieved, is an exact structuring and sizing of the implant site SI such that the same may receive the dental implant ID thereby ensuring stability thereof.

The method of the invention provides to perform a calculation step f2 of a prosthetic axis PI ideal for the dental prostheses PD. The ideal prosthetic axis is an axis passing through an ideal point of the dental prosthesis PD provided, depending on the type of tooth which is being treated. In particular, in a first case of molars and premolars (FIG. 5), the ideal prosthetic axis PI for the intended dental prosthesis PD, is formed as an axis passing through the center pt1 of the intended dental prosthesis PD. In particular, in a second case of lateral incisors and canines (FIG. 12), the ideal prosthetic axis PI for the intended dental prosthesis PD, is formed as an axis passing through the palatal vertex pt2 of a triangle that schematizes the occlusal surface of the intended dental prosthesis PD. In other words, in a first case of molars and premolars, the ideal point pt1 will be at the center of the dental prosthesis PD and CO crown, whereas, in a second case of anterior teeth (incisor, lateral and canine), the ideal point pt2 will be at the apex of the palatal angle.

In both cases, for the calculation of that axis, the method provides obtaining two pairs of measures of the simulated dental prosthesis PD, in particular a first pair of cervical measures and a second pair of apical measures which are defined in terms of statistical data dependent on the position of the tooth and the anatomy of the arch opposed to that into which the dental prosthesis PD is inserted. The pair of measures is calculated in the vestibule-lingual and anterior-posterior direction. To be precise, the first pair of measures is taken at the crown of the dental prosthesis PD and in the vestibule-lingual and anterior-posterior direction. The second pair of measures is taken at the collar of the dental prosthesis PD and in the vestibule-lingual and anterior-posterior direction. Alternatively or in addition, the pair of measures is calculated in the mesio-distal direction. Precisely, the first pair of measures is taken at the dental prosthesis crown PD, while the second pair of measures is taken at the level of the collar of the dental prosthesis PD.

The method provides calculating the prosthetic axis PI as a straight line passing through the intersection points of the segments of each measured pair.

Since the OM maxillary bone exhibits a conformation which slightly degrades from the vestibule toward the tongue, it is requested to find the correct bone angle with respect to the tooth. To this end, the method according to the invention provides for the calculation of two axes: the already described ideal prosthetic axis PI and an ideal surgical axis CI, which allows an ideal halving of the maxillary bone OM amount at the edentulous site LR. In particular, as already mentioned, where a PD dental prosthesis is applied to the mandibular arch, the bone OM is disposed below the prosthesis, whilst in the case of a PD dental prosthesis applied to the upper arch, the bone OM is disposed above the prosthesis. In order to accurately determine the ideal surgical axis CI, the method of the invention provides a plurality of detections being representative values of the maxillary bone OM. The technical effect achieved leads to a precise sizing and shape detection of the bone, being necessary for obtaining a precise simulation of an implant site SI that is to be afforded within the bone itself.

In FIG. 3 a dental prosthesis PD with underlying mandibular bone OM thereof is depicted in a sectional view along an A-A' plane transverse to the maxillary bone OM. With particular reference to this figure and to FIG. 1, the method according to the invention provides a calculation step f3 of a first cervical distance CT and a first apical distance ET of the maxillary bone OM relative to, and more particularly, below, the edentulous site LR.

According to the invention, the calculation of these distances is performed as a function of the graphic simulation of the step f2 and in a first direction with respect to the maxillary bone OM. Preferably, the first direction is substantially transverse with respect to the maxillary bone OM. Preferably, the first cervical distance CT is a distance on the Vestibule-Lingual or Vestibule-Palatal plane between the two cortical at the height of the cervical margin of the maxillary crest. In particular, in the case of very thin ridges it is considered a minimum width of at least 4 mm. Preferably, the first apical ET distance is a distance on the Vestibule-Lingual or Vestibule-Palatal plane between the two cortical at the height of the apical margin.

Figure 6:
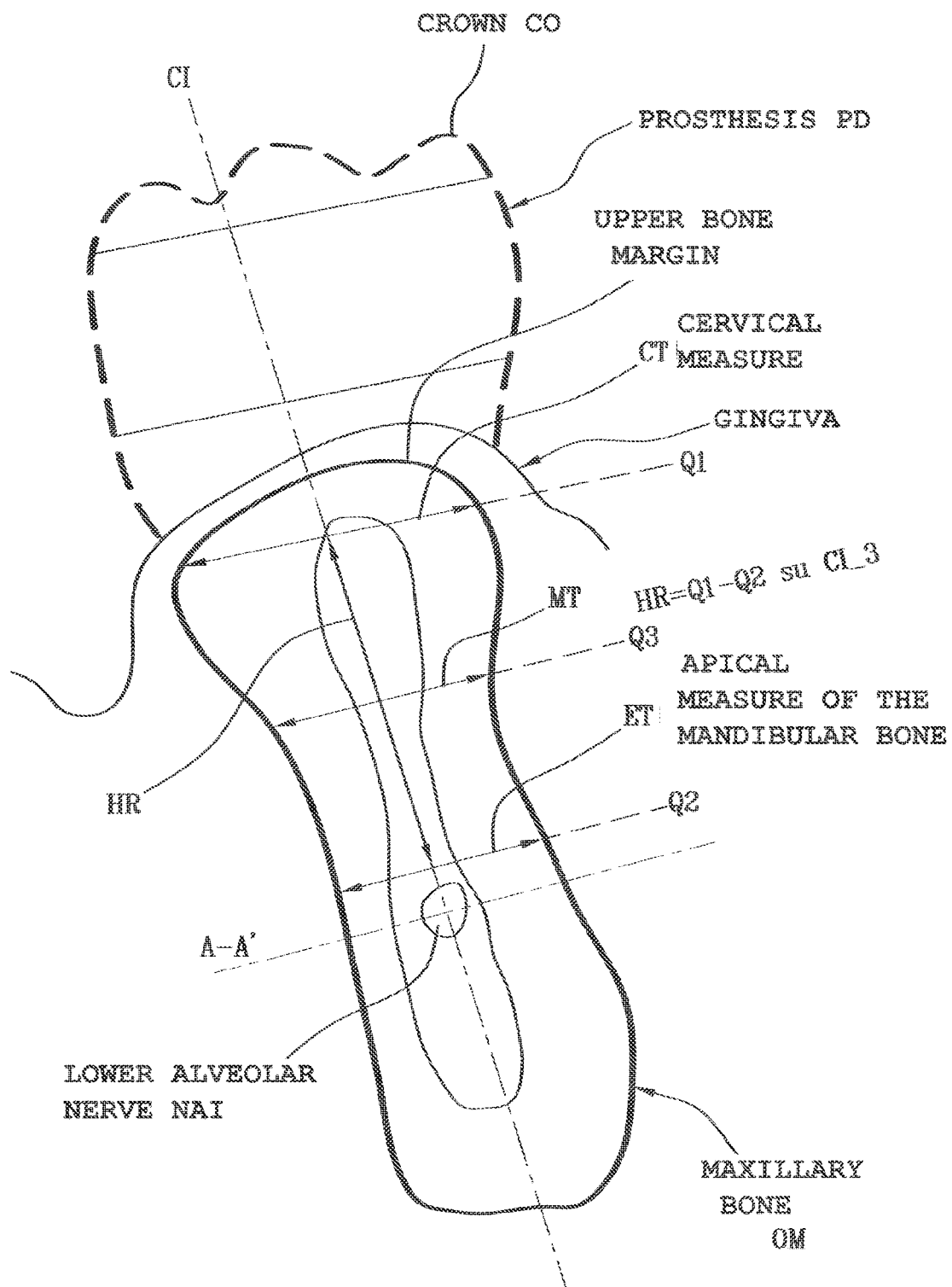
FIG. 6 is a more detailed schematic view of FIG. 5.

According to the invention, the first cervical distance CT is measured at a first cervical portion q1 with respect to a reference portion, for example with respect to the upper edge of the bone shown in FIG. 6. Preferably, in the latter case depicted in FIG. 6, the first cervical portion q1 is identified in reference to the upper margin of the bone crest where the latter is equal to or greater than 4 mm.

According to the invention, the first apical distance ET is detected at a first apical portion q2 with respect to a reference portion, in particular with respect to the lower maxillary nerve NAI in the posterior mandible, or to any other anatomical structure to be observed. Preferably, in the case shown in FIG. 6, the first apical portion q2 is identified above the lower maxillary nerve NAI, preferably at a distance of 2 mm. Alternatively, absent a nerve, the first apical distance ET is detected at a first apical portion q2 with respect to a reference portion, in particular it deals with an anatomical limit comprised between: the lower edge of the mandible (frontally to the NAI for lower arch) and the NAI posteriorly; maxillary sinus and nasal cavity (for upper arch); impacted teeth; cysts; and anatomical defects.

The method according to the invention provides a calculation step f4 of a second cervical distance CW and a second apical distance EW of the maxillary bone OM at, and in particular below the edentulous site LR. According to the invention, the calculation of these distances is made as a function of the step f1 in a second direction with respect to the maxillary bone OM. Preferably, the second direction is substantially longitudinal to the maxillary bone OM. In particular, the second direction is perpendicular to the direction along which the distances CT and ET are calculated. Preferably, the second cervical distance CW is the distance with respect to the bone crest between the limits of the edentulous site LR. In other words, CW is the distance between the roots of the teeth adjacent to the edentulous site LR, where adjacent teeth exist, as shown in the case depicted in FIG. 1.

Figure 15:
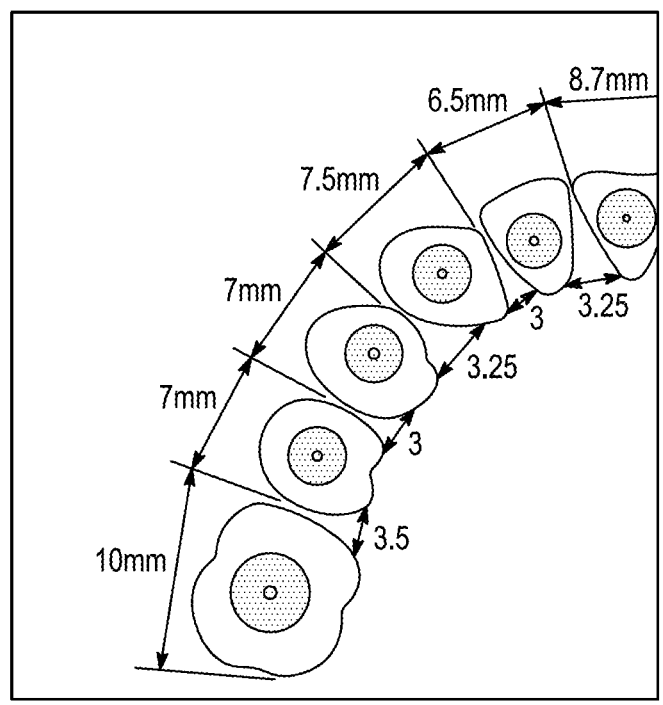
FIG. 15 is a schematic view of a hypothetical positioning of dental implants in relation to the position of the dental elements to be replaced.

Absent the adjacent teeth, the CW calculation is made considering as if the teeth exist, i.e. considering as extremes the continuation into the bone of the planes tangent to the mesial and distal sides of the tooth and perpendicular to the occlusal plane, as shown in FIG. 15. Alternatively, CW is the distance between a root of an adjacent tooth and another implant or anatomical limit.

According to the invention, the second cervical distance CW is detected at the same first cervical portion q1 used for the calculation of CT. According to the invention, the second apical distance EW is detected at the same first apical portion q2 used for the calculation of ET. In other words, CT and CW are measured at the same portion. The technical effect achieved is a schematic regular representation of the irregular anatomy. The same reasoning applies to ET, EW MT and MW. The overall technical effect is that of predisposing a regular volume within an irregular anatomy.

According to the invention, the method comprises the step f5 of calculating an ideal surgical axis (CI_i=1 . . . n) on the maxillary bone OM as a function of cervical distances CT, CW and apical distances CW, EW. In particular, according to the invention, the surgical axis CI is defined as an axis passing through two points, the first Cx obtained as an intersection between the representative segments of the cervical distances CT, CW, and the second Ex obtained as an intersection between the segments representative of the apical distances ET, EW. The surgical axis is calculated in this way both in the case of molars and premolars, as well as in the case of front teeth (incisor, lateral and canine).

According to the invention, the set of references comprising the ideal prosthetic axis PI and the ideal surgical axis CI, determines a reference system REF_ID (FIG. 9) to the dental implant ID, wherein the ideal prosthetic axis PI and the ideal surgical axis CI are offset by a deviation angle α (FIG. 5).

FIG. 4 shows a schematic view of the first and second cervical distances CT, CW, and the first and second apical distances ET, EW and the ideal surgical axis CI obtained as previously described. It is noted from the figure that the y directions along which first distances CT and ET are calculated, are substantially perpendicular to the x directions along which the second distances CW and EW are calculated. The calculated distances are representative of maxillary bone OM volume at the edentulous site LR. The technical effect achieved by the identification of these distances is an identification of the overall dimensions of the maxillary bone OM intended to receive the implant site; the greater the overall dimensions, the greater the maximum diameter of a potential implant insertable into the maxillary bone.

In addition to the steps described above, the method according to the invention provides a calculation step f14 of a first median distance MT measured at a first median portion q3 (FIG. 6) in the maxillary bone OM between the first cervical portion q1 relative to the first cervical distance CT, and the first apical portion q2 relative to the first apical distance ET. Preferably, said first median distance MT is at a median portion q3 that is intermediate between the first cervical portion q1 and the first apical portion q2. The technical effect achieved by this further detection is an identification of the exact shape of the maxillary bone OM that allows detection of malformations (e.g. cavity) in the bone that make the bone unsuitable for housing the implant site.

Alternatively or in addition to the calculation of the first median distance MT, the method according to the invention comprises a step f15 of calculating a second median distance MW measured at the same median portion q3 used for the calculation of MT. The technical effect achieved by this additional measurement is an identification of the exact shape of the maxillary bone OM that allows detection of malformations (e.g. cavity) in the bone that make the bone unsuitable for housing the implant site.

The calculation of the first median distance MT and the second median distance MW is obtainable by the fifth calculation module 105. A further technical effect is achieved when the measurement of the second median distance MW is associated with the measurement of the first median distance MT; in this case the shape of the maxillary bone OM is reconstructed in an even more exact manner, thereby allowing an optimal definition of the overall dimension of the maxillary bone within which the implant site is being obtained. In other words, the median distances MT, MW serve to evaluate the possible presence of a severe anatomical effect, (e.g. a bone lack) which may heavily affect the dental implant diameter.

The inventive method further comprises the step f6 of calculating a bone height HR_i of the maxillary bone OM as a function of the calculated first cervical distance CT and first apical distance ET, as will be described in a later section. The bone height HR is representative of a bone availability of the maxillary bone OM at the edentulous site LR, particularly therebelow. According to the invention, the bone height HR is obtained as the difference on the surgical axis CI_i between the first cervical portion q1 associated with the cervical distance CT, and the first apical portion q2, associated with the apical distance ET. A fifth calculation module 105 of the processing unit 10, described below, is configured to calculate the HR bone height.

The invention further comprises the step f7 of moving the ideal surgical axis CI_i relative to the ideal prosthetic axis PI maintained in a fixed position, thereby resulting in a compromise surgical axis CI_i (i=1 . . . n) corresponding to a deviation angle αi (i=1 . . . n) (FIG. 9) being variable with respect to the ideal prosthetic axis PI. In other words, the method provides moving the ideal surgical axis CI by determining a compromise surgical axis CI_i (i=1 . . . n) corresponding to a deviation angle αi (i=1 . . . n) being variable with respect to the ideal prosthetic axis PI. In other words, the invention method provides for calculating a deviation angle αi (i=1 . . . n) variable between a movable compromise surgical axis CI with (i=1 . . . n), and the ideal prosthetic axis (PI). In yet other words, with reference to FIG. 9, the invention provides moving the surgical ideal axis CI_1 (which subtends a deviation angle α1), towards the ideal prosthetic axis PI maintained in a fixed position, thereby determining a compromise surgical axis CI_2 that subtends a deviation angle α2. The deviation angle αi (i=1 . . . n) is a representative measure of the maxillary bone OM inclination with respect to the dental prosthesis PD provided (i.e. with respect to the ideal prosthetic axis PI thereof); the more the maxillary bone is inclined with respect to the dental prosthesis PD, the more the ideal surgical axis is prevented from passing through the profile of the dental prosthesis, which means that it does not pass through the occlusal surface SO of the tooth.

Figure 9:
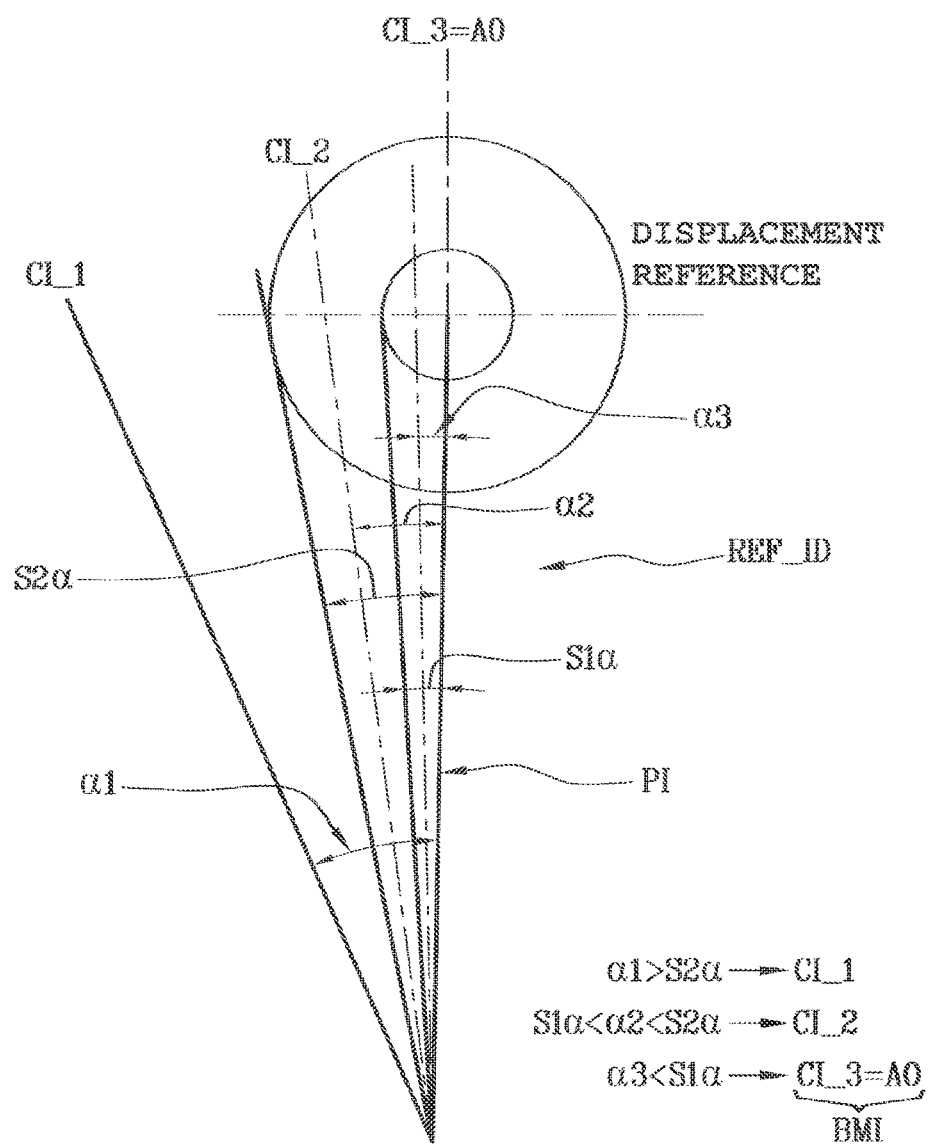
FIG. 9 is a schematic representation of reciprocal positions of ideal surgical axes and a prosthetic axis.

The ideal surgical axis CI_i is moved so as to fall within the profile of the dental prosthesis PD; in FIG. 9 the passing from the surgical axis CI_1 to the surgical axis CI_2, with corresponding passing of the deviation angle varying from α1 to α2, determines a surgical compromise axis which falls within the profile of the dental prosthesis PD.

According to the invention, the calculation of the bone height HR_i of the maxillary bone OM is made both as a function of the already calculated first cervical distance CT and first apical distance ET, and as a function of the variable deviation angle αi (i=1 . . . n). In other words, the more the ideal surgical prosthetic axis CI and the ideal axis PI are proximate to each other, the more the angle α decreases and the bone height value approaches an optimal value. From a mathematical viewpoint, $HR=(q1-q2)/\cos \alpha$, wherein a is=to the angle between the surgical axis CI and the prosthetic axis PI and wherein typically $0°<\alpha<90°$. Since $\cos \alpha<1$ between $0°$ and $90°$, the bone height HR is always smaller than the difference between q1 and q2, except for the case where $\alpha=0$. In other words, the more the ideal CI surgical axis approaches the prosthetic ideal axis PI, the more the angle α decreases, thus resulting in a bone height HR variation.

When determining the bone height HR, the invention provides for the following sizing: the first cervical distance CT must be greater than a first threshold distance S1_CT possibly adjustable, i.e. CT>=S1_CT, wherein S1_CT is preferably=to 4 mm; in other words, S1_CT=4 mm is the minimum value required for a dental implant ID being realized according to the invention without having to resort to a bone augmentation; the first apical distance ET must be greater than a second threshold distance S2_CT, i.e. ET>=S2_CT; in other words, S2_CT=2 mm is taken at the positioned portion q2, preferably, at a distance of 2 mm from a reference portion representative of an anatomical limit; preferably, the anatomical limit is the lower maxillary nerve NAI. The technical effect achieved by the described sizing is to provide an implant site in an optimal position within the bone, so as to avoid any interference with proximal anatomical limits, thereby protecting the integrity of the patient as much as possible.

The invention provides that the values of the distances CT, ET, CW, EW may vary as a function of the variable deviation angle αi (i=1 . . . n). In other words, the values pertaining to: the first cervical distance CT; the first apical distance ET; the second cervical distance CW; the second apical distance EW are defined as a function of each identified single deviation angle αi (I=1 . . . n), thereby being corresponding values CT_i, ET_i, CW EW_i defined.

The invention provides a step f8 of simulating the optimized implant site SI for the dental implant ID in the maxillary bone OM at the edentulous site LR. In one of the main aspects of the invention, which will be described in greater detail below, an implant site simulation system comprises a processing unit 10, in turn comprising a simulation module 107 configured to implement the simulation step f8. The optimized implant site SI exhibits an at least partially cylindrical volumetric shape VSI inscribed within an expected circumscribing volume V.

According to the invention, the optimized implant site SI is simulated at least as a function of: the identified tooth Tn; a first cervical distance CT_i and a first apical distance ET_i; a second cervical distance CWi and a second apical distance EWI; the bone height HR_i; the variable deviation angle αi (i=1 . . . n). In other words, a new implant site is calculated whenever there is a variation in the deviation angle αi, which in turn determines a variation in reference marginal and apical distances and in the bone height. In one embodiment of the invention, the distances CTi, ETI, CWi, EWI are variable depending on the variable deviation angle αi, thereby determining an optimized implant site SI when the variable deviation angle is minimized. The invention therefore provides for calculating implementation values of the optimized implant site SI as a function of the simulation, thereby determining an optimized implant site SI configured to receive the corresponding dental implant ID.

The simulation module 107 is configured in particular to calculate implementation values of the optimized implant site SI as a function of the simulation, thereby determining an optimized implant site configured to receive the corresponding dental implant ID. In particular, the variable deviation angle is minimized when the compromise surgical axis CI_i tends to the ideal surgical axis CI as much as possible, thus ensuring a balance of forces on the PD prosthesis which ensures stability/feasibility thereof.

In a third aspect, the invention comprises, in the first instance, an optimized implant site SI obtained with the method described up to now.

In a fourth aspect, the invention comprises, in the first instance, a dental implant ID which may be coupled to the optimized implant site SI.

The invention further provides a step f12 of comparing the variable deviation angle αi (i=1 . . . n) with the predefined threshold values of the deviation angles S1α, S2α (FIG. 9). The threshold values are representative of a surgical axis CI_i position with respect to an occlusal surface SO of the dental prosthesis PD. In other words, the first deviation threshold value S1α is the greater limit angle of the deviation angle αi (i=1 . . . n) for a definition of an optimized dental implant (Best Matching Implant BMI) otherwise defined as limit inclination angle of the ideal surgical axis CI_i, based on which the angle between the ideal prosthetic axis PI and the ideal CI surgical axis may be considered as minimized. The second deviation threshold value S2α is the greater limit angle of the deviation angle αi (i=1 . . . ne S2a>S1α) such that the ideal surgical axis CI_i passes through the profile of the dental prosthesis PD, that is, passes through the occlusal surface SO of the tooth.

Preferably, the invention provides that the comparison step f10 comprises the steps of: (f6) recalculating bone thickness HR_i; (f7) moving the ideal surgical axis CI_i relative to the ideal prosthetic axis PI_i maintained in a fixed position, thereby resulting in a variation of the variable deviation angle αi (i=1 . . . n).

According to the invention, the steps herein described are performed until the variable deviation angle αi remains incompatible with the predefined deviation angles threshold values of the S1α, S2a. In other words, the steps f6 and f7 are repeated until the condition remains based on which the deviation angle αi is greater than the first deviation threshold value S1α, i.e. αi>S1α). The deviation angle αi (i=1 . . . n) is minimized when is smaller than the first predefined deviation angle threshold values S1α. In other words, when CI_i varies its angle αi relative to the prosthetic axis PI, the distances CT, ET, MT consequently vary the measure thereof, in that the angle varies based on which the segments CT, MT, ET are crossing transversely the maxillary bone OM (i.e. from tongue to vestibule).

The invention provides, at this stage, the step f10 of identifying at least one optimized dental implant within the implant site SI_I as a function of a variable deviation angle $\alpha i$ (i=1 . . . n), compatible with the predefined deviation angle threshold values S1$\alpha$; S2$a$. The values S1$\alpha$, S2$\alpha$ are representative of the passing of the ideal surgical axis CI_i through a portion of the dental prosthesis PD of said occlusal surface SO.

In summary, when S2$\alpha$<$\alpha$i, if CI_i and PI are offset by a variable deviation angle $\alpha$i which is greater than the second predefined threshold value S2$\alpha$, there are generated moments of forces on the prosthesis PD which is to be inserted into the edentulous LR site that may cause a deviation of the PD prosthesis resulting in the prosthesis escaping from the edentulous site LR. Conversely, when S1$\alpha$<$\alpha$i<S2$\alpha$, while not being optimal, the implant position is not even unacceptable since the moments of force acting on the tooth are minimal, thereby remaining the PD prosthesis substantially stable. If CI_i and PI are offset by $\alpha$i<S1$\alpha$, the value $\alpha$i<S1$\alpha$ determines the optimal offset angle $\alpha$OTT between CI and PI. The calculation of the optimal implant site SI takes place at the optimal offset value $\alpha$i.

In the third aspect of the invention, the implant site SI is optimized according to the invention and is representative of the best compromise for the inclination angle of the implant between the extreme positions of the ideal surgical axis CI and the ideal prosthetic axis PI.

According to the invention, the optimized implant site SI achieves the technical effect of enabling the dental implant ID installed therein, to avoid arising of mechanical moments of forces which would result in being unfavorable to the tooth permanence in the edentulous site LR. In fact, because during mastication the masticatory force is along the PI axis, which means that the stress arising therefrom is a compressive stress and not a flexural stress, from a mechanical viewpoint, the PD dental prosthesis should lie on said prosthetic axis PI.

Where the deviation angle between the surgical axis and the prosthetic axis is minimized, there are no moments of force being able to "destabilize" the dental prosthesis, which means that the arm that is created between the ideal surgical axis CI and the prosthetic axis PI has substantially null values. In such a case, the implant site would be suitable to accommodate an implant considered to be optimized.

With reference to FIG. 9, a case of optimal surgical axis is indicated which is referred to with CI_3. In the case where the surgical axis is offset with respect to the prosthetic axis such that the surgical axis is not crossing the profile of the dental prosthesis PD, i.e., it is not passing through the occlusal surface of the tooth, a couple of forces is generated due to the fact that the arm between CI and PI is not null and the resulting implant is not optimal. With reference to FIG. 9, a case of non-optimal surgical axis is indicated by CI_1.

In the fourth aspect of the invention, a dental implant ID may be coupled to the optimized implant site SI obtained as already described. The invention provides simulating the optimized implant site SI (step f8), in which the optimized implant site SI exhibits an at least partially cylindrical volumetric shape VSI inscribed within the circumscribing volume V. The simulation module 107 is configured to simulate the optimized SI implant site in the maxillary bone OM, wherein the optimized implant site SI has an at least partially cylindrical VSI volumetric shape inscribed within an expected circumscribing volume V. In particular, the optimized implant site has a cylindrical shape.

With particular reference to FIGS. 1 and 8, the implant site SI according to the invention, may be calculated as a function of an expected circumscribing volume V having a first dimension L1, a second dimension L2, and a third dimension H. Preferably, the circumscribing volume V is shaped in a first approximation as a parallelepiped.

According to the invention, the first dimension L1 is calculated as a function of at least the first cervical distance CT and the first apical distance ET. Preferably, the first L1 size is defined as the minimum measure between the first cervical distance CT and the first apical distance ET decreased by a predefinable safety margin $\Delta$L1. In other words, L1=min (CT, ET)–$\Delta$L1. In general terms, the value of the first dimension L1 is selectable by the clinician. In particular $\Delta$L1=3 mm.

According to the invention, the second dimension L2 is calculated as a function at least of the second cervical distance CW and second apical distance EW. Preferably, the second dimension L2 is defined as the minimum measure between the second cervical distance CW and the second apical distance EW decreased by a predefinable safety margin $\Delta$L2. In other words, L2=min (CW, EW)–$\Delta$L2. Generally speaking, the value of the first dimension L2 is selectable by the clinician. In particular $\Delta$L2=3 mm.

According to the invention, the third dimension L3 is calculated as a function at least of the bone height HR. In particular, in the example described in the figures, the first dimension L1 is representative of a buccal-lingual distance, the second dimension L2 is representative of a mesial-distal distance, whereas the third L3 dimension is representative of a depth of the optimized implant site at the edentulous site LR, particularly at an underlying zone. In other words, the implant site SI according to the invention is obtainable as cylinder inscribed in the circumscribing volume V.

According to the invention, the calculation of the implant site SI starting from an expected circumscribing volume V, is also made as a function of the first median distance MT and/or the second median distance MW. In other words, according to the invention, the first dimension L1 is calculated as a function of the first cervical distance CT, the first apical distance ET and the first median distance MT.

According to the invention, the second dimension L2 is calculated as a function of the second cervical distance CW of the second apical distance EW and the second median distance MW. The technical effect achieved is the simulation of an implant site entirely compatible with the dimensional and structural characteristics of the receiving maxillary bone OM.

Once the optimized implant site SI has been simulated, the method provides several evaluations based on the parameters being representative of the dental implant ID, which dental implant ID may be coupled to the optimized implant site after calculating the new HR_i and resulting new values of CTi ETI, CWi, EWI, HRi, $\alpha$i, on the basis of the new CI_2 axis.

Figure 10A:
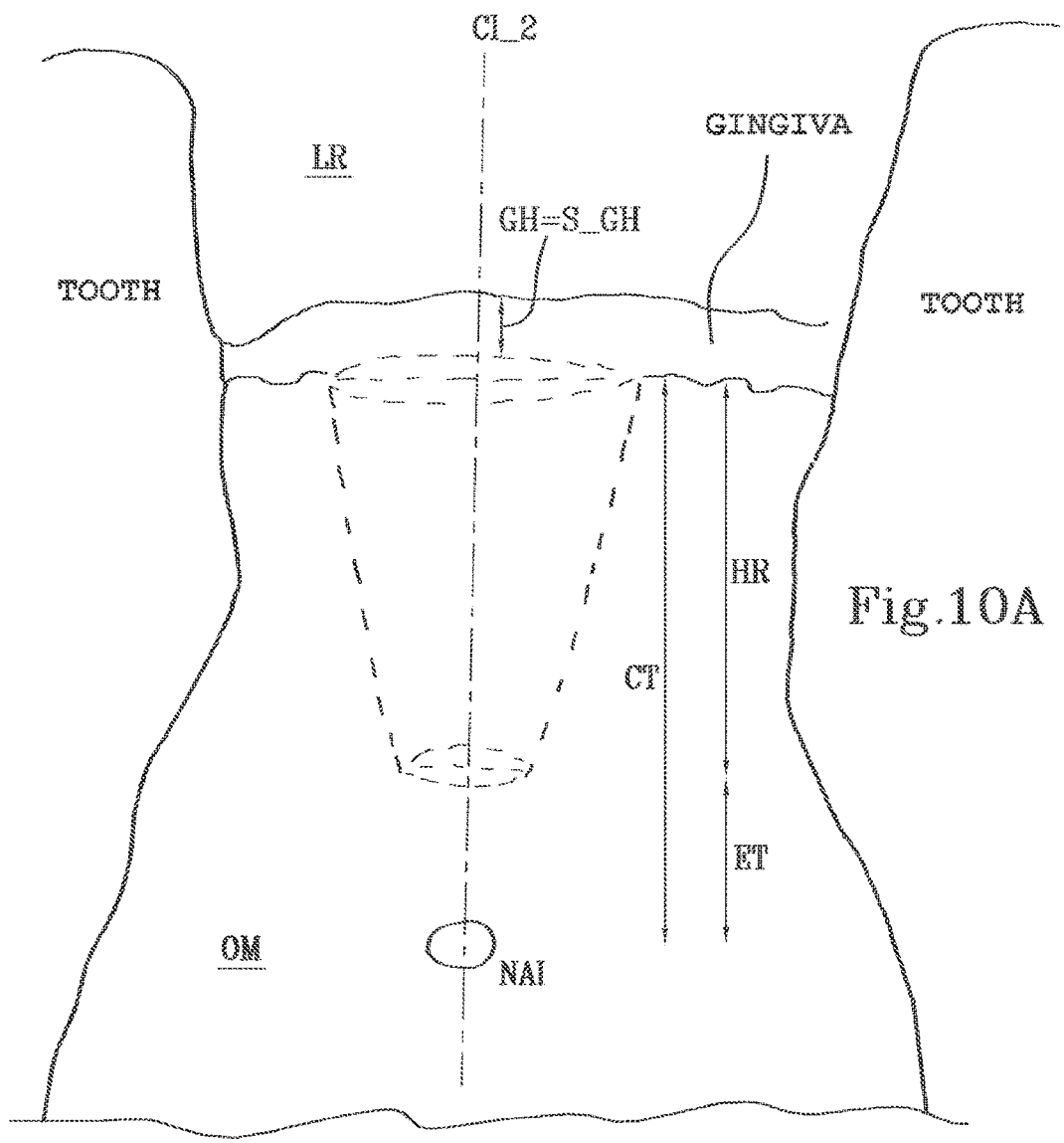
FIGS. 10A, 10B and 10C are schematic views for the evaluation of parameters representative of an optimal dental implant according to the invention.
Figure 10B:
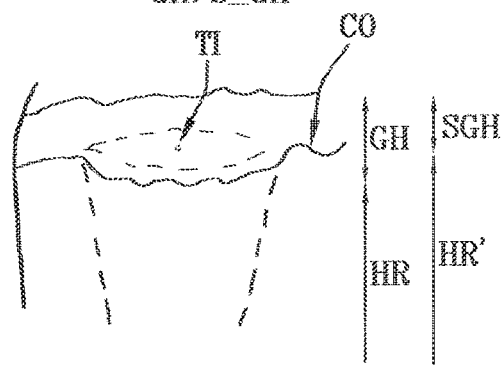
Figure 10C:
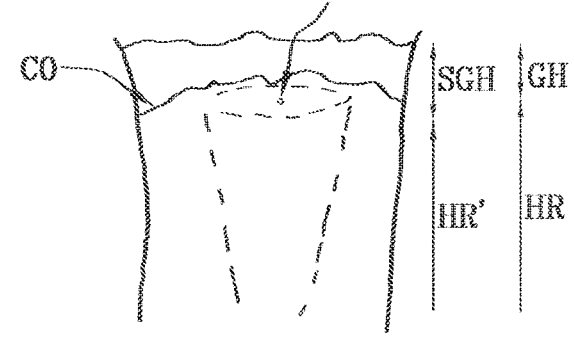
Figure 14:
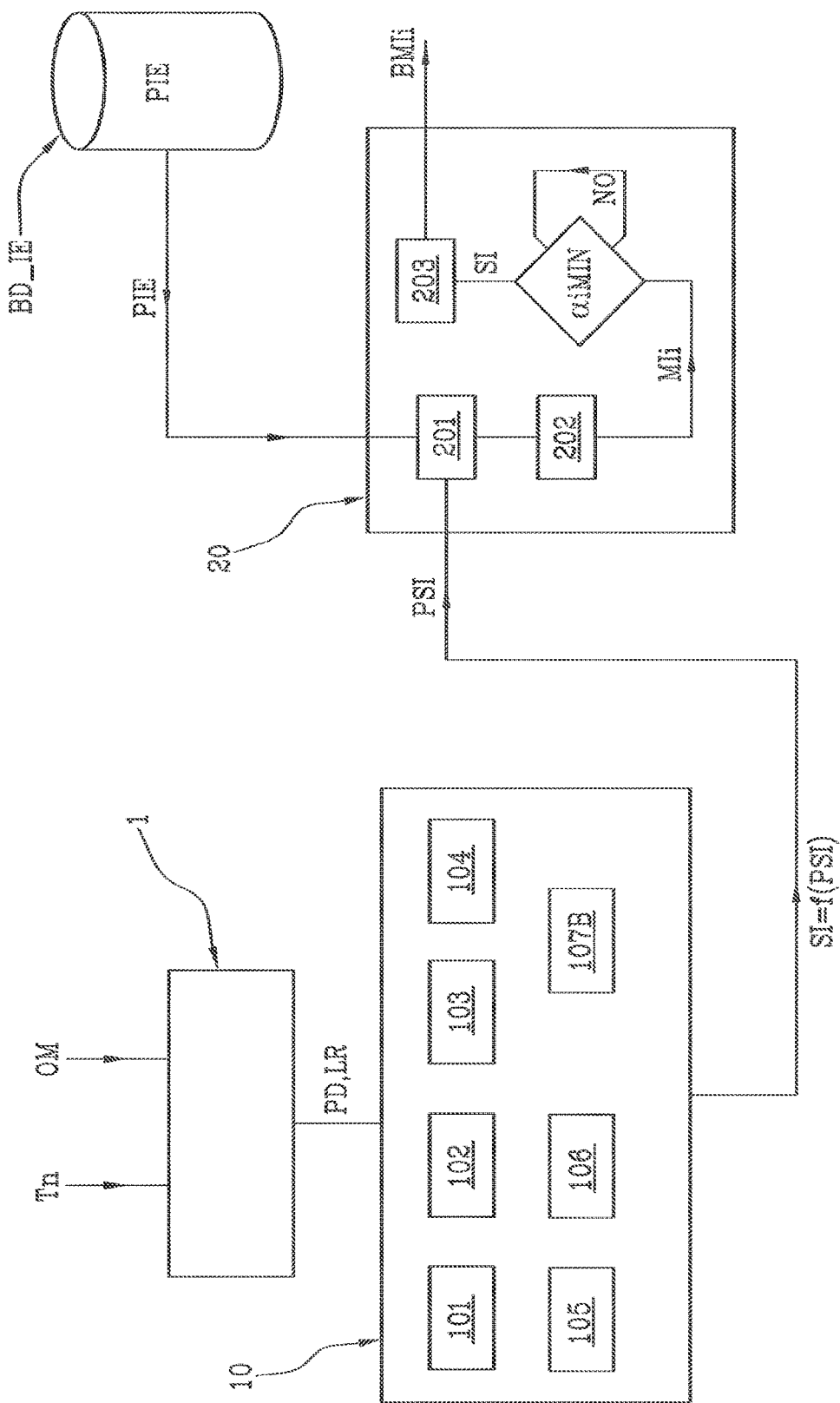
FIG. 14 is a schematic block diagram of a dental implant identification system.

A first parameter to be evaluated is a dental implant (ID) head (TI) position. With reference to the group of FIGS. 10A, 10B and 10C according to the invention, the calculation of the head TI position is made as a function of the gingival height GH being indicative of the gingival thickness above the bone crest CO of the maxillary bone OM along the concerned surgical axis. The head position TI calculation is further made as a function of a predefinable threshold gingival height S_GH, which is also defined as the distance between the maxillary bone OM and the lower part of the dental prosthesis PD. The simulation module 107 is configured to perform calculation of the position of the head TI.

According to the invention, the step of evaluating the position of the head (TI) of the dental implant (ID) comprises the substeps of:

- where the gingival height GH is>than the predefined threshold gingival height S_GH (see FIG. 10B), increasing the bone thickness HR_i with following increase in the first cervical distance CT, or increasing in the height of the crown CO obtained by fixing the position value of the head TI at the value of the first cervical distance CT.
- where the gingival height GH is<than the predefined threshold gingival height S_GH (see FIG. 10C), then calculating a new bone thickness value HR_i and assigning to the first cervical distance CT the new bone thickness value HR_i; in other words, the new bone thickness value HR_i is such that HR_i=HR+GH−S_GH.
- where the gingival height GH is=to the predefined threshold gingival height S_GH, (see FIGS. 10A and 9 with surgical axis CI_3), considering the current bone thickness HR_i as the optimal representative thickness of the correct position of the head TI and storing the value of first current cervical distance CT.

Preferably, 3 mm<S_GH<4 mm. More preferably, S_GH=3.5 mm. Consequently the length of the implant site LI is defined as a function of the bone height calculated HR_i. The simulation module 107 is configured to simulate the implant site SI as a function of the implant site length LI defined as a function of the optimal bone height HR-i.

A second parameter to be evaluated is a measure of a diameter DT of the dental implant head TI. The measure of the DT diameter is calculated as a function of a minimum measure between the distances CT, MT, ET and CW, MW, EW, as a function of a first predefined threshold diameter value S_D1. The simulation module 107 is configured for such calculation.

The method of the invention provides namely the step of determining a measure of a DT diameter of the implant head TI as comprising the substeps of: calculating the minimum measure MIN_L between the distances CT, MT, ET and CW, MW, EW; and calculating the diameter DT as a function of the minimum calculated measure MIN_L and a first predefined threshold diameter value S_D1. The technical effect is achieved based on which the head TI is uncapable of breaking through the buccal peak or lingual peak. In other words, the method allows to determine the diameter of the implant head with the certainty that the implant will definitely be comprised within the maxillary bone, namely the head thereof does not "break through" the buccal or lingual peak. In most cases the minimum measure MIN_L is the first cervical distance CT.

Preferably the diameter DT is calculated as the difference between the calculated minimum measure MIN_L and the first predefined threshold diameter value S_D1. Preferably, such a minimum measure being MIN_L=3 mm. Preferably, the diameter threshold value S_D1 is defined according to the "type" of tooth the implant which is being realized is intended for. These values are defined in the literature, e.g. S_D1>=4.5 in respect to molars and S_D1>=3.5 in respect to premolars. It follows that the optimized implant site SI is implemented as a function of the diameter DT, obtained as the diameter of the cylinder inscribed in the circumscribing volume V, wherein the diameter DT is calculated as a function of the first dimension L1 and second dimension L2.

In particular, the simulation module 107 is configured to simulate the optimized implant site SI according to the aforementioned diameter DT.

The method provides for an evaluation of the compatibility of the diameter measure DT with predefined bone thickness thresholds, in particular a first thickness threshold S_VE calculated with respect to the vestibular peak PV, and a second thickness threshold S_PL calculated with respect to the lingual peak PL. The method particularly provides to determine an optimal implant when the following occurs: the diameter DT is at a distance>=to the first thickness threshold S_VE compared to the vestibular peak PV; and the diameter DT is at a distance>=to the second threshold S_PL thickness compared to the lingual peak PL.

In one preferred embodiment of the invention, the predefined diameter threshold value S_DI is obtained as the sum of the first thickness threshold S_VE and the second threshold thickness S_PL. Preferably S_VE=2 mm. Preferably S_PL=1 mm. The technical effect achieved is that the implant will definitely be comprised within the maxillary bone, substantially centered between the vestibular peak and lingual peak.

A third parameter to be evaluated is a measure of an implant LI length of the dental implant ID. According to the invention, the step of determining the implant LI length is implemented as a function of a recalculated value of the bone thickness HR_i. A fourth parameter to be evaluated is a measure of a crown/root RL/RC ratio. A fifth parameter to be evaluated is an implant percentage in the bone PO. A sixth parameter to be evaluated is a bone density DO, defined as a function of a preset density value HF.

The optimization degree of the implant site SI is evaluated based on a rating (i.e. an evaluation) being assigned to the values of the parameters representative of the simulated implant site. The technical effect achieved is the simulation of an optimal implant site SI to which a plurality of available implants can be compared including selecting the best existing dental implant IE.

The simulation of the optimal implant site SI is implemented as a function of a global rating R of the optimized implant site SI defined as a function of one or more of: a rating of a deviation angle R_αi of said deviation angle αi; a diameter rating R_DT of the diameter DT; a length rating R_LI of the length measure LI of the optimized implant site SI; a crown/root R_RL_RC ratio rating; a percentage rating of the implant in the bone R_PO; a bone density rating R_DO, wherein the rating values Rαi, GDR, RLI, RRLRC, RPO, RDO of the optimized implant site SI are defined as a function of a comparison between the current values αi, DT, LI, RLRC, PO, DO and respective reference thresholds below described.

In one embodiment, the invention provides the step 9 of preparing a database BD_IE (FIG. 11) comprising second representative parameters PIE of existing dental implants IE. The IE existing dental implants are preferably cylinder-shaped while the second representative parameters PIE include diameter and length of the cylinder. Typically the database BD_IE, which possibly may be consulted remotely, includes the second representative parameters PIE being representative of: a tooth identifier (ETN) for an existing implant (IE); an implant diameter (EDTI) for an existing implant (IE); an implant height (ELli) for an existing implant (IE); a deviation angle (Eαi) for an existing implant (IE); a rating identifier (EM) for an existing implant (IE); an implant manufacturer; an implant model.

In one embodiment, the optimized implant site SI is instead calculated at least as a function of its first representative parameters PSI comprising at least: a diameter DTi of the at least partially cylindrical volumetric shape VSI; an height LIi of the at least partially cylindrical volumetric shape VSI; the variable deviation angle αi. The invention provides a step f10 of comparing the first representative parameters PSI with the second representative parameters PIE.

Advantageously, according to the invention, there is provided a step f11 of identifying one or more dental implants MB for the implant site SI optimized as a function of the comparison between the first representative parameters PSI and the second representative parameters PIE.

In step f8 simulating the optimized implant site SI, the first representative parameters PSI further comprise one or more rating values (Rai, GDR, RLI, RRLRC, RPO, RDO) of the optimized implant site SI, defined as a function of a comparison among the first representative parameters PSI and the reference threshold values, which will be described hereinafter.

The optimized implant site SI is identified with an R rating defined in a combined function of the rating values Rai, GDR, RLI, RRLRC, RPO, RDO. In one embodiment, the implant site SI is optimized when the R rating is minimized. According to the invention, the step f11 identifies one or more optimal dental implants BMII as a function of the comparison between the first representative parameters PSI and the second representative parameters PIE when the rating R is minimized. As will be described in more detail below, the identification system of the invention comprises a second processing unit 20 comprising a comparison module 201 configured to compare the first representative parameters PSI with the second representative parameters PIE.

According to the invention, the comparison between the first representative parameters PSI and second representative parameters PIE is made as a function of a different comparison priority Pconf. In other words, certain parameters such as the deviation angle, have a higher incidence on the rating than others.

According to the invention, the comparison between the optimized simulated implant site SI and the existing available dental implants IE, is made as a function of the technical representative parameters of the couplable implant site/dental implant, and the rating values associated with the comparison between these parameters and the corresponding actual values of existing available implants EI. In particular, according to the invention, there is provided the step f13 of assigning a rating R_αi to the dental implant ID as a function of the comparison between the variable deviation angle αi (i=1 ... n) and the predefined deviation angle threshold values S1α, S2α, analyzed in the comparing step f12. For this purpose, as will be described in more detail below, the second processing unit 20 comprises an optimization module 204 configured to perform all the steps of rating assignment to the implant site. The optimal implant BMII according to the invention is the best compromise for the implant deviation angle αi between the extreme positions of the ideal surgical axis CI and the ideal prosthetic axis PI.

According to the invention, a rating is associated to each compromise position; based on the rating calculation dependent on such compromise and further functional dependencies that will be described later in this section, one can determine the optimal way to be adopted for obtaining the BMI. In particular, upon shifting the surgical axis CI toward the prosthetic axis PI, hypothetical dental implants ID_i are identified, which are implementable with a different rating each. More specifically, if αi>S2α→the rating is=−2: the score is unfavorable (case CI_1 of FIG. 9); if S1α<αi<S2α→the rating is=−1 (case CI_2 of FIG. 9); if αi<S1α→the rating is=0 BMI (case CI_3 of FIG. 9). In other words, the step f13 of assigning a rating to the implant site Rai SI is defined as a function of the step f12 of comparing the variable deviation angle αi (i=1 ... n) with predefined deviation angle threshold values S1α, S2a, wherein the rating Rai decreases upon decreasing of the deviation angle αi, and tends to zero when the deviation angle tends to the optimized value thereof.

The invention provides that the step f13 of assigning a rating includes the steps of: (f6) moving the ideal surgical axis (CI_i); (f7) calculating a bone height (HR_i; i=1 ... n) of said bone; (f8) recalculating the distances CT, ET, CW, EW as a function of the variable deviation angle αi (i=1 ... n); identifying a corresponding optimized implant site SI; identifying corresponding dental implants BMIi and corresponding variable rating value R. In a particular embodiment, the step of assigning a rating comprises the steps of: where the rating remains with a value other than, moving the surgical axis (CI, CI_i); calculating a bone height (HR_i; i=1 ... n) of said bone; recalculating (CTi, ETI, CWi, EWI) as a function of the variable deviation angle (αi; i=1 ... n); identifying the corresponding optimal implant site SI; identifying the corresponding optimal dental implants BMI.

In summary, according to the invention, the surgical axis is first defined and subsequently moved progressively towards the prosthetic axis; for each iteration i (i=1 ... n) from the initial position of the surgical axis CI_i (i=1) up to the final position in which said ideal surgical axis CI_i is crossing the occlusal surface SO (e.g. Ci_3), the software defines configuration values CTi, ETI, CWi, EWI, HRi, αi of a corresponding implant site/dental implant of which a rating is calculated. In other words, to each implant site/dental implant defined at least by the configuration values CTi, ETI, CWi, EWI, HRi, αi, a rating is associated by the evaluation software, and the implant with the best rating will then define the BMI. To be noted is the importance of assigning a rating to the surgical axis in all simulated positions in that it is not obvious that the theoretically optimal position (i.e. the one in which the surgical axis CI is substantially coincident with the prosthetic axis PI), is reachable or achievable; it may occur in fact that the particular conformation/shape of the maxillary bone makes not practicable the theoretically optimal implants.

Advantageously, the invention software provides simulating a plurality of theoretically optimal and non-optimal implants, as well as calculating a rating which allows to subsequently define the actual BMI—not necessarily coinciding with the theoretical optimum implant—as a function of the technical and structural characteristics of the bone. The technical effect achieved is determining an optimal dental implant both as a function of a structural logical theoretical calculation and as a function of a calculation of the actual sizing of the technical-structural bone variables.

According to the invention, the first representative parameters PSI and second representative parameters PIE respectively comprise the diameter DTi of the at least partially cylindrical volumetric shape VSI, and the implant diameter EDTI for the existing implant IE, obtained with the substeps of: calculating a minimum measure MIN_L between the distances CT, MT, ET and CW, MW, EW; calculating the diameter DTi, EDTI as a function of the minimum measure MIN_L calculated, and a first predefined diameter threshold value S_D1; checking that DTi or EDTI is at a distance that is >=than a first thickness threshold S_VE compared to the vestibular peak PV; checking that DTi or EDTi is at a distance being>=than a second thickness threshold S_PL compared to the lingual peak PL.

The invention provides to assign a rating to the measure of a diameter DTi or EDTI wherein: if the diameter DTi or EDTI is <the second predefined value of threshold diameter S_D2, then→the rating is=to −1; if the diameter DTi or EDTI is<than the third predefined value of threshold diameter S_D3, then→the rating is=to −2. Preferably, the second predefined value of threshold diameter S_D2 is=to 0.2 mm for premolars. Preferably, the third predefined value of threshold diameter S_D3 is=to 0.5 mm for premolars. According to the invention, the first representative parameters PSI and the second representative parameters PIE respectively comprise the height LII of the at least partially cylindrical volumetric shape and the implant height ELli for the existing implant IE, obtained as a function of a value of the bone height HR_i.

The invention provides to assign a rating to the height measure LII, ELli as a function of a first predefined value of threshold height SL_1. If LI is>than the first predefined value of threshold length (SL_1), then→the rating is=to −2. If LI is<than the first predefined value of the threshold length (SL_1), then→the rating is=to −1. Preferably, SL_1 is=to 2 mm. The preferred values are defined according to the type of tooth and the reference literature.

According to the invention, the first representative parameters PSI and the second representative parameters PIE include a crown/root ratio RL_RC. The invention provides to assign a rating R_R1_RC to the crown/root ratio RL_RC, wherein if RL/CL is >=with respect to a first threshold SRLRC1, (in particular=1), then→the rating is=to 0; if RL/CL is <SRLRC1, then→the rating is −1; if RL/CL is <SRLRC2<SRLRC1, then→the rating is −2. Preferably, SRLRC1=1; Preferably, SRLRC2=0.75.

In particular, if RL/CL is >=1, then→the rating is=to 0; in other words, if the root length RL is>than the crown length CL, the rating is=to 0 in that the technical effect of a more stable tooth is attained. If 0.75 is <RL/CL<1, then→the rating is −1; In other words, if the length of the root RL is<than the crown length CL, the tooth is more unstable. If RL/CL is <0.75, then→the rating is −2, thus resulting in the tooth to be even more unstable.

According to the invention, the first representative parameters PSI and the second representative parameters PIE comprise a implant percentage PO in the maxillary bone OM. The invention provides to assign a rating R_PO to the implant percentage PO in the bone; if PO is=to 100%, then→the rating is=to 0; if a first threshold PO1 is <PO<than a second threshold PO2, then→the rating is −1; If PO is<than the first threshold PO1, then→the rating is −2. Preferably, the first threshold PO1 is=to 95%. Preferably, the second threshold PO2 is=to 99%.

According to the invention, the first representative parameters PSI and second representative parameters PIE include a bone density DO. The invention provides to assign a rating R_DO to the bone density PO, wherein: if DO is>than the threshold density SDO, then→the rating is=to 0; if I DO is<than the threshold density SDO, then→the rating is=to −1. According to the invention, the simulation module 107 is configured to simulate the optimized implant site SI as a function of one or more of: the crown/root ratio; the implant percentage within the bone PO,—the density DO of the maxillary bone OM; the global rating R of the optimized implant site SI.

In a second aspect, the present invention describes a computer implemented simulation method of an implant site as described above. In a third aspect, the invention comprises, in a first analysis, an optimized implant site SI obtained with the method described up to now, as previously indicated. In a fourth aspect, the invention comprises, in a first analysis, a dental implant ID couplable to the optimized implant site SI as previously already mentioned. In a fifth aspect, the present invention describes a computer program configured to perform one or more steps of the computer implemented method when running. In a sixth aspect, the present invention describes a simulation system of an implant site.

Figure 12:
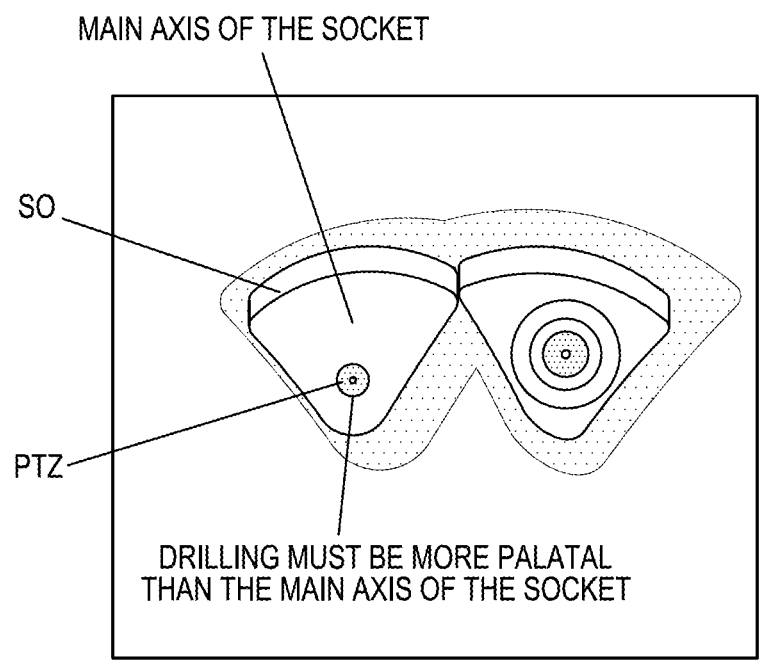
FIG. 12 is a schematic plan view of the incisor teeth.

The system will now be described with reference to FIG. 12. The simulation system of an optimized implant site SI comprises: computer-implemented simulation graphics means 1 configured to graphically simulate an anatomy of a dental prosthesis PD provided, and a respective edentulous site LR, both corresponding to an identified tooth Tn, wherein said dental prosthesis PD provided, is couplable to a dental implant ID insertable into a maxillary bone OM; a processing unit 10 configured to simulate an optimized implant site starting from the simulation of the anatomy of the intended dental prosthesis PD, comprising:

a first calculation module 101 configured to calculate an ideal prosthetic axis PI for the intended dental prosthesis PD as a function of said simulation wherein the ideal prosthetic axis PI is an axis crossing an ideal point of the envisaged PD dental prosthesis as a function of the type of tooth Tn considered;

a second calculation module 102 configured to calculate a first cervical distance CT and a first apical distance ET of said maxillary bone OM at said edentulous site LR as a function of said graphic simulation, wherein the distances are calculated in a first direction with respect to said maxillary bone OM. Preferably, the first direction is substantially transverse to the maxillary bone OM.

a third calculation module 103 configured to calculate a second cervical distance CW and a second apical distance EW of said maxillary bone OM at said edentulous site LR as a function of said graphic simulation, wherein the distances are calculated in a second direction with respect to the maxillary bone OM. Preferably, the second direction is substantially longitudinal to the maxillary bone OM.

a fourth calculation module 104 configured to calculate an ideal surgical axis CI on said maxillary bone OM as a function of said cervical distances CT, CW and said apical distances CW, EW wherein said ideal surgical axis (CI) is an axis configured to perform an ideal halving of the bone quantity of the maxillary bone (OM) at the edentulous site (LR), wherein the ideal prosthetic axis PI and the ideal surgical axis CI determine a reference system REF_ID for said dental implant ID; wherein said ideal prosthetic axis PI and said surgical ideal axis CI are offset by a deviation angle $\alpha$;

a fifth calculation module 105 configured to calculate a bone height HR of said maxillary bone OM as a function of said calculated first cervical distance CT and first apical distance ET, wherein said bone height HR is representative of a bone availability of said maxillary bone OM at said edentulous site LR;

a handling module 106 configured to move said ideal surgical axis CI, thereby determining a compromise surgical axis CI_i; i=1 . . . n corresponding to a variable deviation angle $\alpha i$ (i=1 . . . n) with respect to said ideal prosthetic axis PI;

a simulation module 107 configured to simulate said optimized implant site SI in said maxillary bone OM, wherein said optimized implant site (SI) exhibits an at least partially cylindrical volumetric shape (VSI) inscribed within a circumscribing volume (V) provided, said simulation being performed at least as a function of: said identified tooth Tn; said first cervical distance CTi and a said first apical distance ETI; said second cervical distance CWi and a said second apical distance EWI; said first bone height HRi; said variable deviation angle $\alpha i$; wherein said first cervical distance CTi, first apical distance ETI, second cervical distance CWi, second apical distance EWI and first bone height HRi are variable as a function of said variable deviation angle, thereby determining said optimized implant site SI when said variable deviation angle $\alpha i$ is minimized.

The system further comprises all memory and/or operational means and/or modules needed to implement the functions described in the method of the invention. Generally speaking, it should be noted that in the present context and in the subsequent claims, the processing unit 10 is presented as divided into distinct functional modules (memory modules or operational modules) for the sole purpose of describing the functionality thereof in a clear and complete manner. Actually, this processing unit may be constituted by a single electronic device suitably programmed to perform the functions described, whilst the different modules may correspond to hardware and/or software entities routines forming part of the programmed device. Alternatively or in addition, such functionalities may be performed by a plurality of electronic devices, whereon aforesaid functional modules can be distributed. The processing unit may further make use of one or more processors for executing the instructions contained in the memory modules. Based on the network architecture wherein they reside, the above functional modules may further be distributed over several computers, locally or remotely. The systems further comprise all means and/or memory and/or operational modules requested to implement the functions illustrated in the respective methods herein described.

A simulation method/system of an implant site has been herein disclosed. The invention confers the main technical effect arising from simulating a specific implant site in terms of sizing and position, and capable of ensuring installable dental implant stability. The simulation performed by the invention achieves technical functions typical of modern engineering work. It provides for realistic prediction of the performance of a dental implant in respect to the designed implant site which shall accommodate the former, and thereby ideally allows the dental implant to be developed so accurately such that a prototype's chances of success can be assessed before it is built. The technical result increases with the speed of the simulation method, as this enables a wide range of designs to be virtually tested and examined for suitability before the expensive implant fabrication process starts. The technical effect of this result is increased consistent with the speed of the simulation method, as this allows a wide range of projects to be tested and virtually examined such that matching thereof may be evaluated prior to beginning the dental implant manufacturing process.

Without a suitable technical support, an advanced test on a complex dental implant and/or a careful selection among many different projects would not be possible, or at least not feasible within a reasonable time. It follows that computer-implemented simulation methods for virtual testing represent a practical and practice-oriented part of the dentist's or healthcare professional's or treatment provider's toolkit. What makes them so important is the fact that there isn't a purely mathematical, theoretical or mental method which is capable of providing a complete and/or fast prediction of a dental implant performance according to the parameters of the invention that is different or diversifiable for each single patient. The invention as described herein particularly achieves the technical effects of: simulating a specific implant site in terms of structure and design; simulating an objective implant site in terms of design; simulating an implant site ensuring installable dental implant stability; easy simulation of an implant site.

The invention claimed is:

1. A computer-implemented method for simulating an optimized dental implant site, the method comprising:
   graphically simulating via a computer-implemented graphic simulation an anatomy of a provided dental prosthesis and a respective edentulous site corresponding to an identified tooth, wherein said provided dental prosthesis is couplable to a dental implant that is insertable into a maxillary bone; and
   calculating an axis and a volume for said provided dental prosthesis that simulates said optimized implant site in said maxillary bone,
   wherein said optimized implant site has an at least partially cylindrical volumetric shape inscribed within a circumscribing volume,
   wherein said simulation is performed as a function of at least said identified tooth, a cervical distance, an apical distance, a bone height, and a variable deviation angle,
   wherein each of said cervical distance, said apical distance, and said bone height varies as a function of said variable deviation angle, and
   wherein said optimized implant site is simulated by varying said variable deviation angle.

2. The method according to claim 1, further comprising:
   graphically simulating via the computer-implemented graphic simulation an edentulous site corresponding to the identified tooth;
   calculating an ideal prosthetic axis for said provided dental prosthesis as a function of said simulation wherein said ideal prosthetic axis is an axis crossing an ideal point of the provided dental prosthesis as a function of the identified tooth;
   calculating the cervical distance and the apical distance at said edentulous site as a function of said graphic simulation, wherein the cervical distance and the apical distance are calculated in a first direction relative to said maxillary bone, and wherein said cervical distance is detected at a first cervical height with respect to a reference height;
   calculating an ideal surgical axis on said maxillary bone as a function of said cervical distance and said apical distance, wherein said ideal surgical axis is an axis configured to perform an ideal halving of the bone quantity of the maxillary bone at the edentulous site, wherein the ideal prosthetic axis and the ideal surgical axis define a reference system for said dental implant, and wherein said ideal prosthetic axis and said ideal surgical axis are offset by the deviation angle;
   calculating the bone height of said maxillary bone as a function of said calculated cervical distance and apical distance, wherein said bone height is representative of a bone availability of said maxillary bone at said edentulous site; and moving said ideal surgical axis so as to determine a surgical compromise axis corresponding to a variable deviation angle with respect to said ideal prosthetic axis.

3. The method according to claim 1, further comprising: calculating implementation values associated with said optimized implant site based on said simulation, to thereby define an optimized implant site that is configured to receive said dental implant.

4. The method according to claim 1, wherein said circumscribing volume has a first dimension, a second dimension, and a third dimension, and
wherein simulating said optimized implant site comprises calculating said first dimension as a function of at least said cervical distance and said apical distance, and calculating said second dimension as a function of at least said bone height.

5. The method according to claim 4, wherein said optimized implant site is simulated as a function of a diameter of a cylinder inscribed within the circumscribing volume, wherein said diameter is calculated as a function of at least said first dimension.

6. The method according to claim 5, wherein simulating said optimized implant site comprises calculating a position of a head of the dental implant as a function of a gingival height and a predefined gingiva height threshold.

7. The method according to claim 5, wherein said optimized implant site is simulated as a function of a length of the implant site defined as a function of the bone height.

8. The method according to claim 1, wherein the simulation of said optimized implant site is further performed as a function of at least one of a crown/root ratio, a percentage of implant within the maxillary bone, a density of the maxillary bone, or a global rating of said optimized implant site.

9. A system for simulating an optimized implant site, the system comprising:
a computer-implemented graphic simulator that is configured to graphically simulate an anatomy of a provided dental prosthesis and a respective edentulous site corresponding to an identified tooth, wherein said provided dental prosthesis is couplable to a dental implant that is insertable into a maxillary bone;
a processing unit configured to simulate an optimized implant site starting from the simulation of the anatomy of the provided dental prosthesis, wherein the processing unit comprises:
a first calculation module configured to calculate an ideal prosthetic axis for the provided dental prosthesis as a function of said simulation, wherein said ideal prosthetic axis is an axis crossing an ideal point of the provided dental prosthesis according to the identified tooth;
a second calculation module configured to calculate a cervical distance and an apical distance of said maxillary bone at said edentulous site as a function of said graphical simulation, wherein the cervical distance and the apical distance are calculated in a first direction relative to said maxillary bone, wherein said cervical distance is detected at a cervical height relative to a reference height;
a third calculation module configured to calculate an ideal surgical axis on said maxillary bone as a function of said cervical distance and of said apical distance, wherein said ideal surgical axis is an axis configured to perform an ideal halving of the bone quantity of the maxillary bone at the edentulous site, wherein the ideal prosthetic axis and the ideal surgical axis define a reference system for said dental implant, and wherein said ideal prosthetic axis and said ideal surgical axis are offset by a deviation angle;
a fourth calculation module configured to calculate a bone height of said maxillary bone as a function of said calculated cervical distance and apical distance, wherein said bone height is representative of a bone availability of said maxillary bone at said edentulous site;
a movement module configured to move said ideal surgical axis by determining a compromise surgical axis corresponding to a variable deviation angle with respect to said ideal prosthetic axis; and
a simulation module configured to simulate said optimized implant site in said maxillary bone, wherein said optimized implant site has at least a partially cylindrical volumetric shape inscribed within an expected circumscribing volume, said simulation being performed as a function of at least said identified tooth, said cervical distance, said apical distance, said bone height, and said variable deviation angle;
wherein said cervical distance, said apical distance, and said bone height are variable as a function of said variable deviation angle, and wherein said optimized implant site is determined by varying said variable deviation angle.

10. The system according claim 9, wherein said simulation module is configured to calculate implementation values of said optimized implant site as a function of said simulation, to thereby define an optimized implant site that is configured to receive said dental implant.

11. The system according to claim 10, wherein said provided circumscribing volume has a first dimension and a second dimension, and
wherein said simulation module is configured to simulate said optimized implant site by calculating said first dimension as a function of at least said cervical distance and said apical distance, and said second dimension as a function of at least said bone height.

12. The system according to claim 11, wherein said simulation module is configured to simulate said optimized implant site as a function of a diameter of a cylinder inscribed within the circumscribing volume, wherein said diameter is calculated as a function of at least said first dimension.

13. The system according to claim 11, wherein said simulation module is configured to calculate a position of a head of the dental implant as a function of a gingival height and a predefined gingiva height threshold.

14. The system according to claim 11, wherein said simulation module is configured to simulate said implant site as a function of an implant site length defined as a function of an optimal bone height.

15. The system according to claim 11, wherein said first dimension is representative of either a vestibular-lingual distance or a mesio-distal distance, and said second dimension is representative of a depth of said optimized implant site.

16. The system according to claim 9, wherein said fourth calculation module is configured to calculate said bone height as a calculation of a distance on the ideal surgical axis between a cervical height that is associated with a cervical distance of said maxillary bone and an apical height that is associated with an apical distance of said maxillary bone.

17. The system according to claim 9, wherein said fourth calculation module is configured to calculate a median distance measured at a median height in the maxillary bone between a cervical height relative to the cervical distance and an apical height relative to the apical distance.

18. The system according to claim 17, wherein said simulation module is configured to simulate said optimized implant site as a function of at least said median distance.

19. The system according to claim 12, wherein said simulation module is further configured to simulate said optimized implant site as a function of said diameter.

20. The system according to claim 9, wherein said simulation module is configured to simulate said optimized implant site based on at least one of:
- a crown/root ratio;
- a percentage of implant within the bone;
- a density of the maxillary bone; or
- a global rating of said optimized implant site.

\* \* \* \* \*